(12) United States Patent
Liu et al.

(10) Patent No.: US 12,042,236 B2
(45) Date of Patent: Jul. 23, 2024

(54) TOUCHSCREEN USER INTERFACE FOR INTERACTING WITH A VIRTUAL MODEL

(71) Applicant: INTUITIVE SURGICAL OPERATIONS, INC., Sunnyvale, CA (US)

(72) Inventors: Wen Pei Liu, San Jose, CA (US); Wendy Chan, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/959,929

(22) Filed: Oct. 4, 2022

(65) Prior Publication Data

US 2023/0031641 A1 Feb. 2, 2023

Related U.S. Application Data

(63) Continuation of application No. 16/635,855, filed as application No. PCT/US2018/044412 on Jul. 30, 2018, now Pat. No. 11,497,569.
(Continued)

(51) Int. Cl.
*G06F 3/0482* (2013.01)
*A61B 5/00* (2006.01)
(Continued)

(52) U.S. Cl.
CPC ............ *A61B 34/35* (2016.02); *A61B 5/7435* (2013.01); *A61B 5/7455* (2013.01); *A61B 34/10* (2016.02);
(Continued)

(58) Field of Classification Search
CPC .................................................. G06F 3/048–05
See application file for complete search history.

(56) References Cited

U.S. PATENT DOCUMENTS

| 5,835,079 A | * | 11/1998 | Shieh | G06F 3/0488 345/157 |
| 7,859,519 B2 | * | 12/2010 | Tulbert | G06F 3/0425 345/173 |

(Continued)

FOREIGN PATENT DOCUMENTS

| CN | 103034436 A | 4/2013 |
| KR | 20100027543 A | 3/2010 |

(Continued)

OTHER PUBLICATIONS

Extended European Search Report for Application No. EP18841648.1 mailed on Apr. 13, 2021, 10 pages.
(Continued)

*Primary Examiner* — Daniel Rodriguez
(74) *Attorney, Agent, or Firm* — Haynes & Boone, LLP

(57) ABSTRACT

Methods and systems are provided that can include accessing a three-dimensional (3D) model of an object with a visualization tool including a touchscreen, displaying, via the touchscreen, an image of the 3D model, detecting a pressure based and/or contact based input at the touchscreen, and changing a display parameter of a first component of the 3D model as a result of the input. Selecting the component and/or changing the display can be indicated by visual and/or haptic signals. A method is provided that can include selectively making components of the 3D model transparent or non-transparent, and changing a center of rotation of the 3D model based on the remaining non-transparent components. A method is provided that can include identifying
(Continued)

gestures of a selection tool via a stereo camera and changing display parameters based on the detected gesture(s).

11 Claims, 32 Drawing Sheets

Related U.S. Application Data

(60) Provisional application No. 62/539,849, filed on Aug. 1, 2017.

(51) Int. Cl.
*A61B 34/10* (2016.01)
*A61B 34/35* (2016.01)
*G06F 3/041* (2006.01)
*G06F 3/04842* (2022.01)
*G06F 3/0488* (2022.01)

(52) U.S. Cl.
CPC ...... *G06F 3/04146* (2019.05); *G06F 3/04842* (2013.01); *G06F 3/0488* (2013.01); *A61B 2034/101* (2016.02); *G06F 2203/04806* (2013.01); *G06F 2203/04808* (2013.01)

(56) References Cited

U.S. PATENT DOCUMENTS

| | | | | |
|---|---|---|---|---|
| 8,314,790 B1* | 11/2012 | Zeiger | G06T 19/00 | 345/592 |
| 8,334,867 B1* | 12/2012 | Davidson | G06F 3/04845 | 715/848 |
| 9,146,674 B2 | 9/2015 | Karlsson et al. | | |
| 9,244,562 B1* | 1/2016 | Rosenberg | G06F 3/04883 | |
| 10,156,921 B1 | 12/2018 | Smith | | |
| 2008/0180406 A1* | 7/2008 | Han | G06F 3/04883 | 345/173 |
| 2010/0039393 A1* | 2/2010 | Pratt | G06F 3/0414 | 345/173 |
| 2010/0110025 A1* | 5/2010 | Lim | G08C 21/00 | 345/173 |
| 2011/0007000 A1* | 1/2011 | Lim | G06F 3/03547 | 345/173 |
| 2011/0296351 A1* | 12/2011 | Ewing, Jr. | G06F 3/04815 | 715/854 |
| 2012/0026100 A1* | 2/2012 | Migos | G06F 3/0412 | 345/173 |
| 2012/0081359 A1* | 4/2012 | Lee | G06F 3/04815 | 345/173 |
| 2012/0159364 A1* | 6/2012 | Hyun | G06F 3/04815 | 715/848 |
| 2012/0159391 A1* | 6/2012 | Berry | A61B 5/4824 | 715/823 |
| 2012/0182296 A1* | 7/2012 | Han | G06F 3/04883 | 715/810 |
| 2012/0242652 A1* | 9/2012 | Kim | G06F 3/0488 | 345/419 |
| 2012/0304122 A1 | 11/2012 | Cordes et al. | | |
| 2014/0009402 A1* | 1/2014 | Ma | G06F 3/04815 | 345/173 |
| 2014/0151853 A1 | 6/2014 | Ohmi et al. | | |
| 2014/0208248 A1* | 7/2014 | Davidson | G06F 3/0483 | 715/766 |
| 2014/0208271 A1* | 7/2014 | Bell | G06F 3/0487 | 715/836 |
| 2015/0082181 A1* | 3/2015 | Ames | G06F 3/04815 | 715/738 |
| 2015/0301661 A1* | 10/2015 | Leigh | G06F 3/047 | 345/174 |
| 2015/0355769 A1* | 12/2015 | Kim | G06F 3/0488 | 345/174 |
| 2015/0363980 A1* | 12/2015 | Dorta | G06F 3/04883 | 345/419 |
| 2016/0018957 A1* | 1/2016 | Wilson | G06F 3/0483 | 715/776 |
| 2016/0188181 A1* | 6/2016 | Smith | G06F 3/04886 | 715/765 |
| 2017/0024061 A1* | 1/2017 | Forlines | G06F 3/0446 | |
| 2017/0140169 A1* | 5/2017 | Boger | G06F 3/04886 | |
| 2017/0220170 A1* | 8/2017 | Sah | G06F 3/04186 | |
| 2017/0220241 A1* | 8/2017 | Vangapalli | G06F 3/041 | |
| 2017/0255378 A1* | 9/2017 | Desai | G06F 3/04883 | |
| 2018/0052575 A1* | 2/2018 | Van Der Westhuizen | G06F 3/0484 | |
| 2018/0121000 A1* | 5/2018 | Klein | G06F 3/0488 | |
| 2018/0157382 A1* | 6/2018 | Nomura | G06F 3/04886 | |
| 2019/0012059 A1* | 1/2019 | Kwon | G06F 3/0481 | |
| 2020/0205914 A1 | 7/2020 | Liu | | |

FOREIGN PATENT DOCUMENTS

KR 20150068330 A 6/2015
WO WO-2011123669 A1 10/2011

OTHER PUBLICATIONS

International Preliminary Report on Patentability for Application No. PCT/US2018/044412, mailed on Feb. 13, 2020, 11 pages.
International Search Report and Written Opinion for Application No. PCT/US2018/044412, mailed on Jan. 21, 2019, 16 pages (ISRG11110/PCT).
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

Taro Yamada     ARE YOU SURE? [−]

DOB: Jul. 9, 1963 (54yo)
Study Date: Aug. 4, 2012 —106

Order Date: Jun. 13, 2017
Order Number: SEG0001016

— 100

Taro Yamada     UNDO 4s [↶]

DOB: Jul. 9, 1963 (54yo)
Study Date: Aug. 4, 2012 —106

Order Date: Jun. 13, 2017
Order Number: SEG0001016

— 102

Taro Yamada     UNDO 1s [↶]

DOB: Jul. 9, 1963 (54yo)
Study Date: Aug. 4, 2012 —106

Order Date: Jun. 13, 2017
Order Number: SEG0001016

TOUCHSCREEN USER INTERFACE FOR INTERACTING WITH A VIRTUAL MODEL

CROSS-REFERENCE TO RELATED APPLICATIONS

This patent application is a continuation of U.S. patent application Ser. No. 16/635,855, filed Jan. 31, 2020, which is the U.S. national phase of International Application No. PCT/US2018/044412, filed Jul. 30, 2018, which designated the U.S. and claims priority to and the benefit of U.S. Provisional Application 62/539,849, filed Aug. 1, 2017, all of which are incorporated by reference herein in their entirety.

FIELD

The present disclosure is directed to systems and methods for navigating through a virtual three-dimensional (3D) model and interacting with components of the 3D model via a touchscreen user interface of a visualization tool.

BACKGROUND

Virtual 3D models can be used to investigate complex systems. Various software applications including computer-aided design (CAD) software can be used to produce virtual 3D models of a variety of complex systems including vehicle assemblies/subassemblies, building structures, robotic systems, and anatomic systems/subsystems. Anatomic 3D models of an object or system, such as a human anatomy and/or portions of a human anatomy, can be produced from images obtained from imaging systems including, for example computed tomography (CT) systems or magnetic resonance imaging (MRI) systems. The 3D models can be comprised of components including layers, sub-assemblies, systems, parts, portions or other subdivisions of the model. For example, layers of the object stacked together may be used to construct the overall 3D model.

A user can interact with a 3D model via a display device to perform various tasks such as interrogating the dimensions of the components of the model as they relate spatially with other components in the 3D model, evaluating interconnections of the components with each other, zooming image in or out to change the level of displayed detail, evaluating anomalies (especially when the object is a human body), assessing routes, and accessing clearances. Generally, this type of interaction is performed through computer mouse inputs, track ball inputs, and the like to navigate around the 3D model via interaction of the input device(s) with multiple nested drop-down or pop-up menus. This interaction generally requires interaction with a user input device separate from the display device. It can be seen that improvements in the art of interacting with a plurality of components of a 3D model is continually needed.

SUMMARY

The embodiments of the invention are summarized by the claims that follow the description.

In one embodiment, a method is provided that can include accessing a three-dimensional (3D) model of an object with a visualization tool including a touchscreen, displaying, via the touchscreen, an image of the 3D model, detecting a pressure based and/or contact based input at the touchscreen, and changing a display parameter of a first component of the 3D model as a result of the input. Selecting the component and/or changing the display can be indicated by visual and/or haptic signals.

In another embodiment, a method is provided that can include accessing a three-dimensional (3D) model of an object with a visualization tool having a touchscreen, the 3D model comprising first and second components; displaying, via the touchscreen, an image of the first and second components, detecting a first contact based input at the touchscreen, selecting the first component in response to the first contact based input, displaying a first icon on the touchscreen, the first icon representing a location on the touchscreen of the first contact based input, displaying second and third icons on the touchscreen in response to the first contact based input, detecting movement of the first contact based input along the touchscreen, tracking movement of the first icon with the movement of the first contact based input, determining from the tracked movement that the first icon at least partially overlaps one of the second and third icons, selecting a display parameter of the first component in response to the overlap determination, detecting a second contact based input at the touchscreen, and adjusting the selected display parameter in response to a detected movement of the second contact based input along the touchscreen.

In another embodiment, a method is provided that can include accessing a three-dimensional (3D) model of an object with a visualization tool including a touchscreen, the 3D model comprising a plurality of components, displaying, via the touchscreen, an image of a subset of the components, wherein in the subset of the components includes each one of the components of the 3D model with a transparency of less than 100%, detecting a first contact based input at the touchscreen, displaying a first icon on the touchscreen, the first icon representing a location on the touchscreen of the first contact based input, detecting movement of the first contact based input along the touchscreen with the first icon tracking the movement of the first contact based input, and responsive to the detected movement, rotating the subset of the components about a center of rotation.

In another embodiment, a method is provided that can include accessing a three-dimensional (3D) model of an object with a visualization tool including a touchscreen, the 3D model comprising first and second components, displaying, via the touchscreen, an image of the first and second components, detecting a first contact based input at the touchscreen, displaying a first icon on the touchscreen, the first icon representing a location on the touchscreen of the first contact based input, detecting a second contact based input at the touchscreen, displaying a second icon on the touchscreen, the second icon representing a location on the touchscreen of the second contact based input, and adjusting a display parameter of the image in response to movement of the first and second contact based inputs on the touchscreen.

In another embodiment, a method is provided that can include accessing a three-dimensional (3D) model of an object with a visualization tool including a touchscreen and a stereo camera, the 3D model comprising first and second components, displaying, via the touchscreen, an image of the first and second components, detecting, via the stereo camera, a first gesture input, selecting the first component in response to the first gesture, detecting, via the stereo camera, a second gesture input, and adjusting a display parameter of the image in response to the detecting of the second gesture.

In another embodiment, a system for interacting with a 3D model is provided that can include a visualization tool with a touchscreen, and a control system including one or more processors, the control system configured to: access a three-dimensional (3D) model of an object with the visualization tool, display, via the touchscreen, an image of the 3D model, detect a first pressure based input at the touchscreen, and change a display parameter of a first component of the 3D model as a result of the first pressure based input.

In another embodiment, a system for interacting with a 3D model is provided that can include a visualization tool with a touchscreen, and a control system including one or more processors, the control system configured to: access a three-dimensional (3D) model of an object with the visualization tool, the 3D model comprising first and second components, display, via the touchscreen, an image of the first and second components, detect a first contact based input at the touchscreen, select the first component in response to the first contact based input, display a first icon on the touchscreen, the first icon representing a location on the touchscreen of the first contact based input, display second and third icons on the touchscreen in response to the first contact based input, detect movement of the first contact based input along the touchscreen, track movement of the first icon with the movement of the first contact based input, determine from the tracked movement that the first icon at least partially overlaps one of the second and third icons, select a display parameter of the first component in response to the overlap, detect a second contact based input at the touchscreen, and adjust the selected display parameter in response to a detected movement of the second contact based input along the touchscreen.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 19 is a representative progressive view of a 3D model entry fading away as the entry is being removed from the 3D model according to some embodiments.

DETAILED DESCRIPTION

Figure 1A:
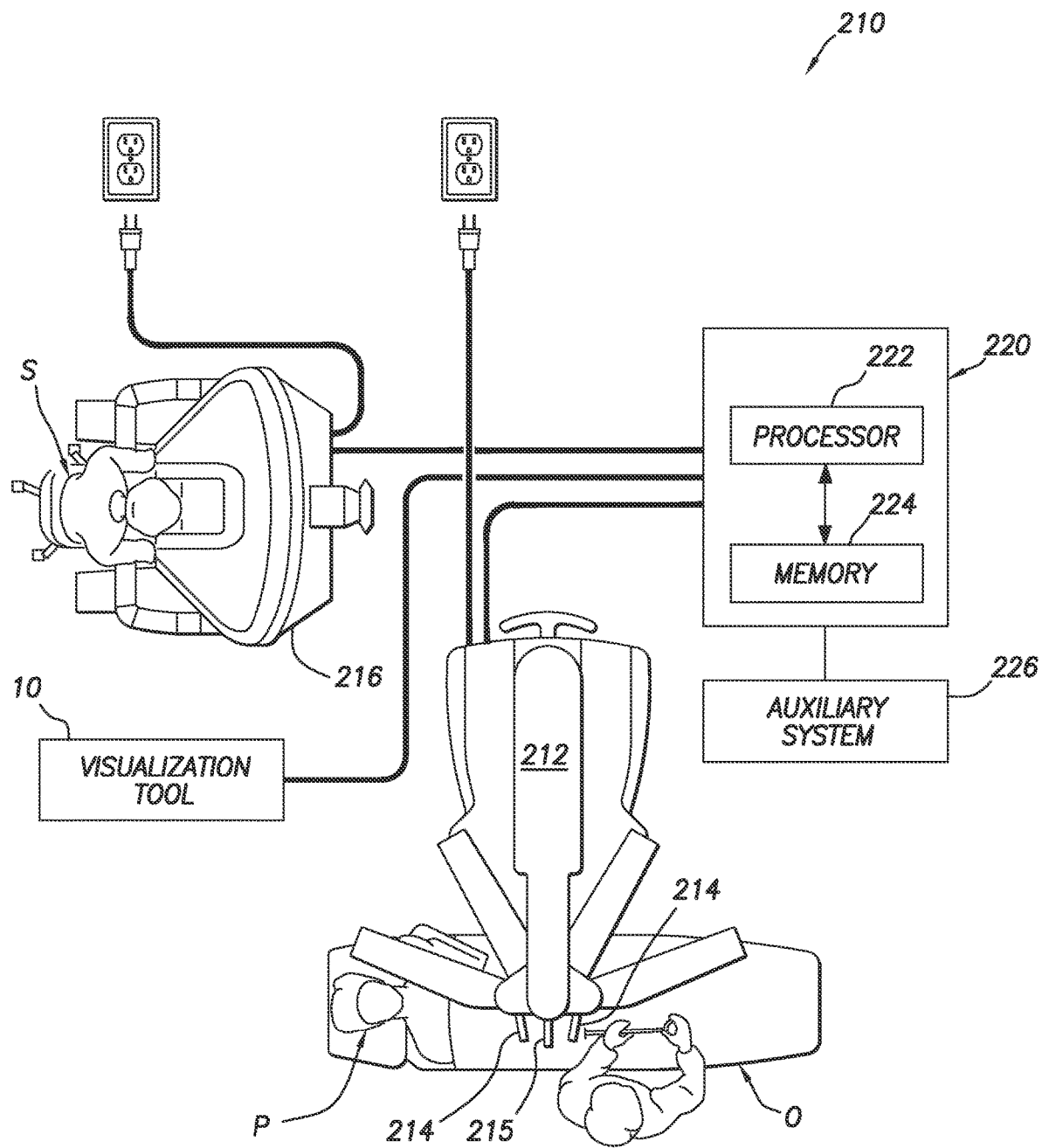
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below may describe objects in terms of their state in three-dimensional space (whether real or virtual space). As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

As used herein, these terms "position," "orientation." "pose." and "shape" can also refer similarly to a virtual three-dimensional (3D) model viewed via a visualization tool that can display the virtual 3D model of an object and/or assembly (such as a human body, human body systems, a vehicle assembly, an airplane assembly, a manufactured assembly, and any other object or assembly that can benefit from a viewable 3D virtual model of the physical entity). As used herein, "component" refers to a portion or subdivision of the 3D model of the object which can include layers, sub-assemblies, subsystems, and any combination of layers, sub-assemblies, and subsystems.

As described in further detail, anatomic 3D models may, for example, be used with teleoperational medical systems to assist with procedure planning, site investigation, and tissue interaction. Referring to FIG. 1A of the drawings, a teleoperational medical system for use in, for example, medical procedures including diagnostic, therapeutic, or surgical procedures, is generally indicated by the reference numeral 210. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 210 generally includes a teleoperational assembly 212 mounted to or near an operating table O on which a patient P is positioned. The teleoperational assembly 212 may be referred to as a patient side cart. A medical instrument system 214 and an endoscopic imaging system 215 are operably coupled to the teleoperational assembly 212. An operator input system 216 allows a surgeon or other type of clinician S to view images of or representing the surgical site and to control the operation of the medical instrument system 214 and/or the endoscopic imaging system 215.

The operator input system 216 may be located at a surgeon's console, which is usually located in the same room as operating table O. It should be understood, however, that the surgeon S can be located in a different room or a completely different building from the patient P. In various embodiments, a teleoperational medical system may include more than one operator input system 216 and surgeon's console. In various embodiments, an operator input system may be available on a mobile communication device including a tablet or a laptop computer. A visualization tool 10 with a touchscreen can be used to interact with a 3D model of an object (in this example the object can be the anatomy of patient P) for viewing 3D renderings of anatomic systems and organs of the patient P. Operator input system 216 generally includes one or more control device(s) for controlling the medical instrument system 214. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like.

In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 212 supports and manipulates the medical instrument system 214 while the surgeon S views the surgical site through the console 216. An image of the surgical site can be obtained by the endoscopic imaging system 215, such as a stereoscopic endoscope, which can be manipulated by the teleoperational assembly 212 to orient the endoscope 215. A control system 220 can be used to process the images of the surgical site for subsequent display to the surgeon S through the surgeon's console 216. The number of medical instrument systems 214 used at one time will generally depend on the diagnostic or surgical procedure and the space constraints within the operating room among other factors. The teleoperational assembly 212 may include a kinematic structure of one or more non-servo controlled links (e.g., one or more links that may be manually positioned and locked in place, generally referred to as a set-up structure) and a teleoperational manipulator.

The teleoperational assembly 212 includes a plurality of motors that drive inputs on the medical instrument system 214. These motors move in response to commands from the control system (e.g., control system 220). The motors include drive systems which when coupled to the medical instrument system 214 may advance the medical instrument into a naturally or surgically created anatomical orifice.

Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 214 may include end effectors having a single working member such as a scalpel, a blunt blade, an optical fiber, or an electrode. Other end effectors may include, for example, forceps, graspers, scissors, or clip appliers.

The teleoperational medical system 210 also includes a control system 220. The control system 220 includes at least one memory 224 and at least one processor 222, and typically a plurality of processors, for effecting control between the medical instrument system 214, the operator input system 216, and other auxiliary systems 226 which may include, for example, imaging systems, audio systems (including an intercom system), fluid delivery systems, display systems, mobile vision carts, illumination systems, steering control systems, irrigation systems, and/or suction systems. Optionally, the visualization tool 10 may also be communicatively coupled to the control system 220 for obtaining stored images or models and/or for integrating the function of the visualization tool 10 with other components of the medical system 210, including the surgeon's console 216. The control system 220 also includes programmed instructions (e.g., a computer-readable medium storing the instructions) to implement some or all of the methods described in accordance with aspects disclosed herein. While control system 220 is shown as a single block in the simplified schematic of FIG. 1A, the system may include two or more data processing circuits with one portion of the processing optionally being performed on or adjacent the teleoperational assembly 212, another portion of the processing being performed at the operator input system 216, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 220 supports wireless communication protocols such as Bluetooth, IrDA, HomeRF, IEEE 802.11, DECT, and Wireless Telemetry.

In some embodiments, control system 220 may include one or more servo controllers that receive force and/or torque feedback from the medical instrument system 214. Responsive to the feedback, the servo controllers transmit signals to the operator input system 216. The servo controller(s) may also transmit signals instructing teleoperational assembly 212 to move the medical instrument system(s) 214 and/or endoscopic imaging system 215 which extend into an internal surgical site within the patient body via openings in the body. Any suitable conventional or specialized servo controller may be used. A servo controller may be separate from, or integrated with, teleoperational assembly 212. In some embodiments, the servo controller and teleoperational assembly are provided as part of a teleoperational arm cart positioned adjacent to the patient's body.

The control system 220 can be coupled with the endoscope 215 and can include a processor to process captured images for subsequent display, such as to a surgeon on the surgeon's console, or on another suitable display located locally and/or remotely. For example, where a stereoscopic endoscope is used, the control system 220 can process the captured images to present the surgeon with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
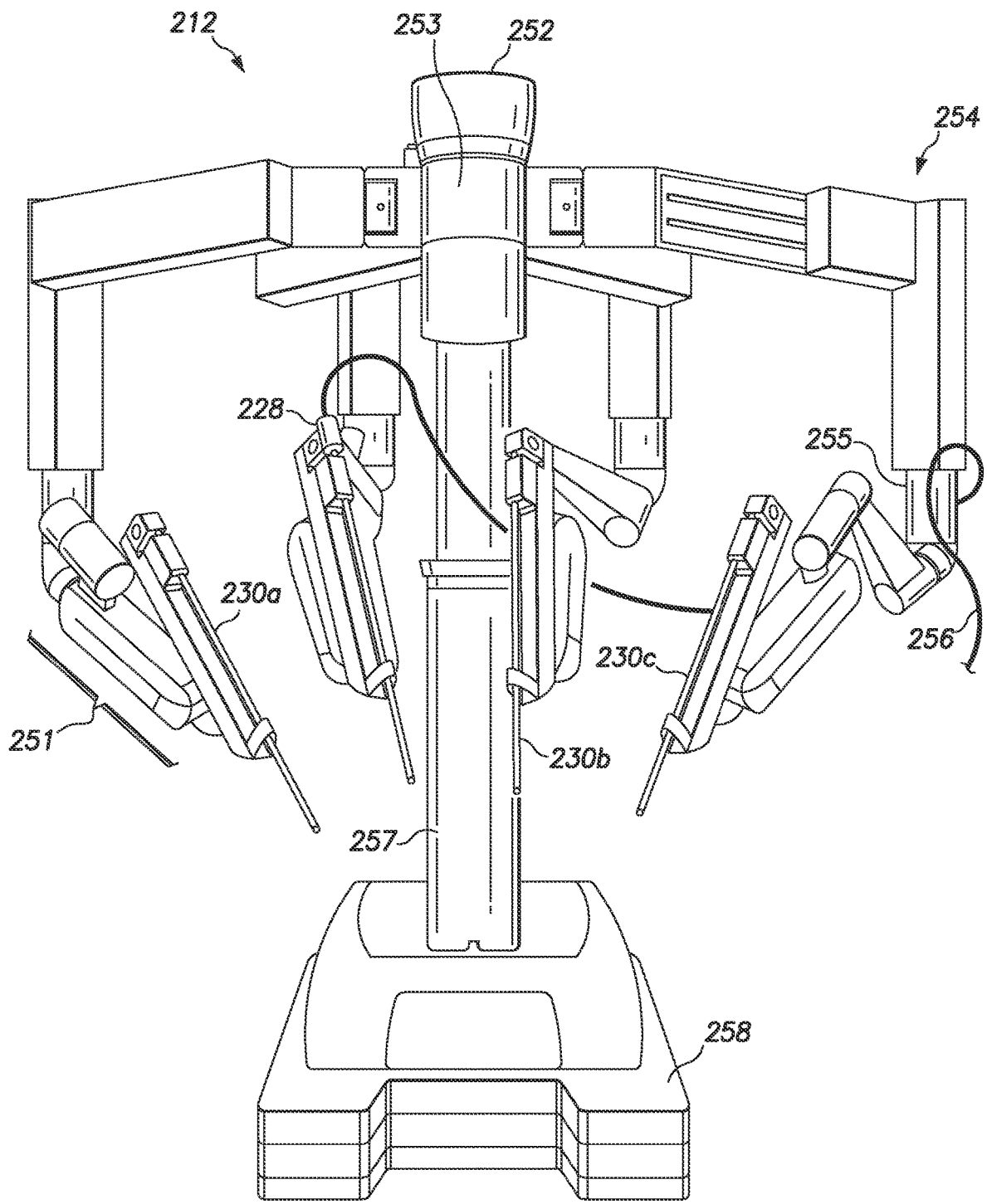
FIG. 1B is a representative perspective view of a patient side cart, according to one example of principles described herein.

FIG. 1B is a perspective view of one embodiment of a teleoperational assembly 212 which may be referred to as a patient side cart. The patient side cart 212 provides for the manipulation of three surgical tools 230a, 230b, 230c (e.g., instrument systems 214) and an imaging device 228 (e.g., endoscopic imaging system 215), such as a stereoscopic endoscope used for the capture of images of the site of the procedure. The imaging device may transmit signals over a cable 256 to the control system 220. Manipulation is provided by teleoperative mechanisms having a number of joints. The imaging device 228 and the surgical tools 230a-c can be positioned and manipulated through incisions in the patient so that a kinematic remote center is maintained at the incision to minimize the size of the incision. Images of the surgical site can include images of the distal ends of the surgical tools 230a-c when they are positioned within the field-of-view of the imaging device 228.

The patient side cart 212 includes a drivable base 258. The drivable base 258 is connected to a telescoping column 257, which allows for adjustment of the height of the arms 254. The arms 254 may include a rotating joint 255 that both rotates and moves up and down. Each of the arms 254 may be connected to an orienting platform 253. The orienting platform 253 may be capable of 360 degrees of rotation. The patient side cart 212 may also include a telescoping horizontal cantilever 252 for moving the orienting platform 253 in a horizontal direction.

In the present example, each of the arms 254 connects to a manipulator arm 251. The manipulator arms 251 may connect directly to a medical instrument 230a. The manipulator arms 251 may be teleoperatable. In some examples, the arms 254 connecting to the orienting platform are not teleoperatable. Rather, such arms 254 are positioned as desired before the surgeon 18 begins operation with the teleoperative components.

Endoscopic imaging systems (e.g., systems 215, 228) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
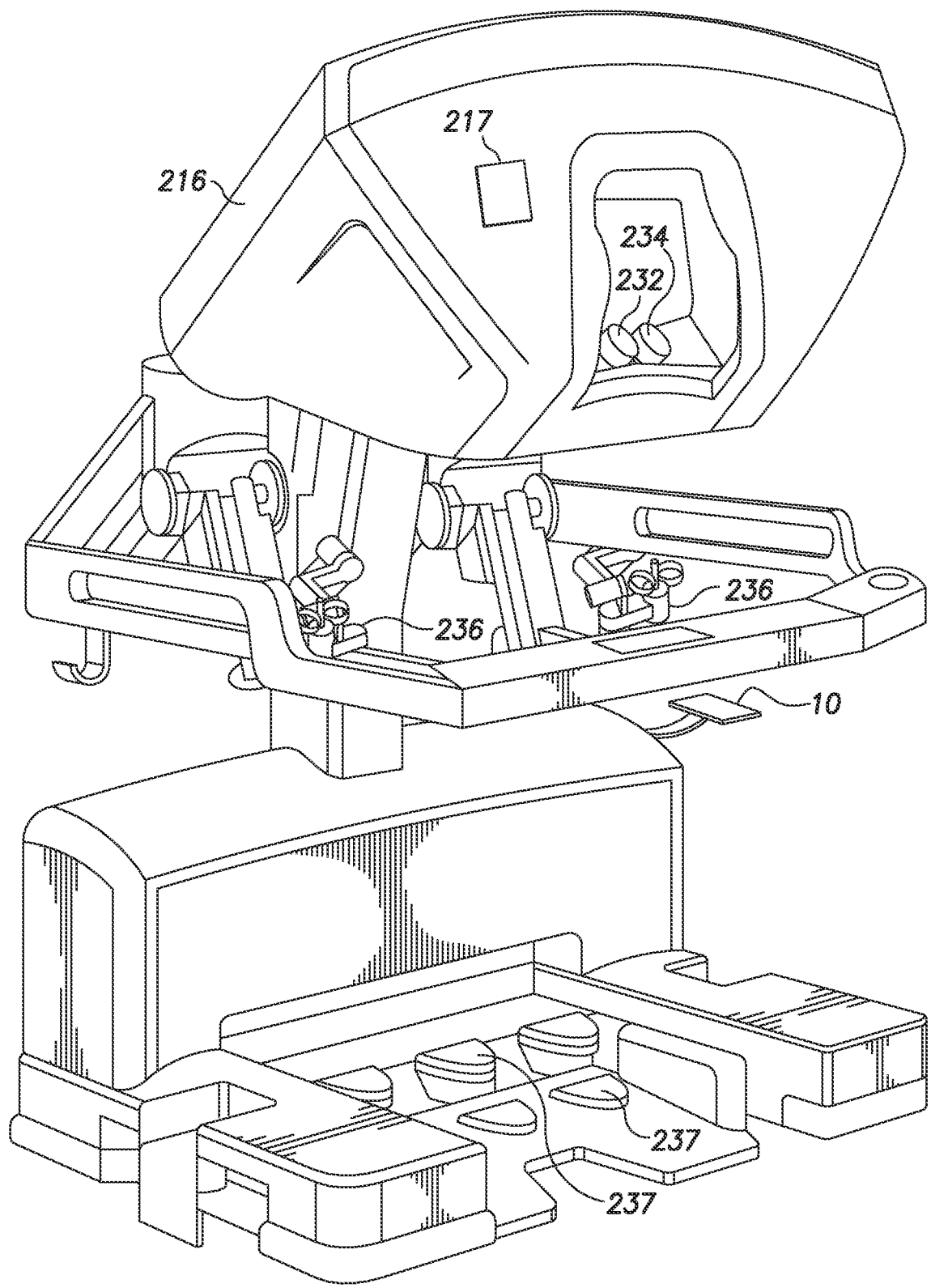
FIG. 1C is a representative perspective view of a surgeon's control console for a teleoperational medical system, in accordance with an embodiment of the present disclosure.

FIG. 1C is a perspective view of the surgeon's console 216. The surgeon's console 216 includes a left eye display 232 and a right eye display 234 for presenting the surgeon S with a coordinated stereo view of the surgical environment that enables depth perception. The console 216 further includes one or more input control devices 236, which in turn cause the teleoperational assembly 212 to manipulate one or more instruments or the endoscopic imaging system. The input control devices 236 can provide the same degrees of freedom as their associated instruments 214 to provide the surgeon S with telepresence, or the perception that the input control devices 236 are integral with the instruments 214 so that the surgeon has a strong sense of directly controlling the instruments 214. To this end, position, force, and tactile feedback sensors (not shown) may be employed to transmit position, force, and tactile sensations from the instruments 214 back to the surgeon's hands through the input control devices 236. Input control devices 237 are foot pedals that receive input from a user's foot.

During a teleoperational procedure, a surgeon may require additional information, may need assistance with equipment or instrument, or may seek guidance in problem-solving. Current trouble-shooting or information gathering techniques require a surgeon to suspend the surgical activity to seek information or resolve problems. For example, if the surgeon is encountering limitations or resistance in the medical instrument while engaged with the operator console 216, the surgeon may need to interrupt the surgical procedure, move away from the operator console, release the control devices 236 to access on-line troubleshooting menus or manuals, or otherwise delay the procedure and introduce associated risk.

The visualization tool 10 can be mounted to the station 216 in a position proximate the surgeon S or clinician to facilitate interaction with a 3D model being displayed on the tool 10. FIG. 1C shows a tool 10 mounted to one side of the console 216. However, the tool 10 can be mounted to another side of the console 216, it can be mounted to a separate floor stand, it can be mounted to a nearby wall of the operating room, it can be mounted to an articulating arm that is attached a suitable portion of the console 216, etc. It should be understood that the tool 10 can be mounted in any suitable configuration that supports the tool 10 in a position that is convenient for the surgeon S to access the tool 10 without having to remove his head from the console to reach and manipulate the tool 10. The image of the 3D model on the tool 10 can be duplicated as an image (such as a picture-in-picture PIP) in a separate window within the image presented to the surgeon S through the eye displays 232, 234. The visualization tool 10, allows the surgeon to interact with the 3D model via the touchscreen without having to look away from the surgeon's console 216 to view the image on the visualization tool 10.

Figure 1D:
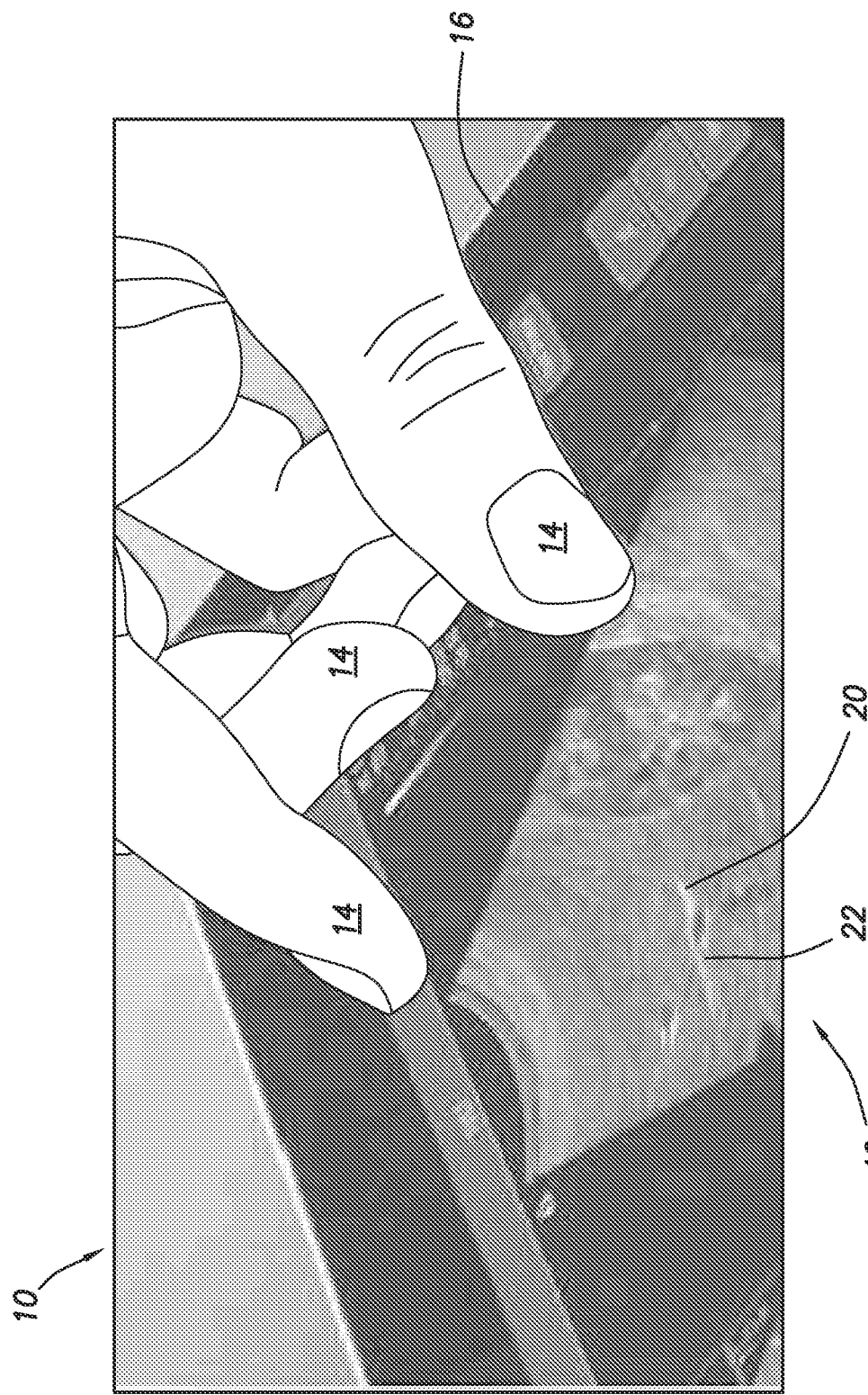
FIG. 1D is a representative perspective view of a visualization device, including a touchscreen, that can be used with a control console for a teleoperational medical system, in accordance with an embodiment of the present disclosure.

FIG. 1D illustrates a representative visualization tool 10 in the form of a computing device 16 with a touchscreen 20. The computing device 16 may be a tablet, laptop, or other mobile device and may communicate with the components of the medical system 210 via wireless or wired communication. The device 16 may also include a variety of sensors including touch-based sensors, strain sensors, movement sensors (e.g., a gyroscope), capacitive sensors, and a stereo camera for detection of motion around the device. In some embodiments, the device 16 may also include a motor, for example, to generate a vibration signal. In some embodiments, the device 16 may also include a gyroscope for generating and/or tracking location, angle of the device 16, etc. An image 22 can be displayed on the touchscreen 20. A user can interact with the displayed image 22 by using his digits 14 to interact with the touchscreen 20. By providing pressure based, contact based, and/or gesture based inputs to the computing device through the touchscreen 20 (and possibly a stereo camera), the user can interact with a 3D model 40 being displayed by the visualization tool 10, to rotate the image 22, expand and contract the image 22, adjust transparencies of various components of the 3D model between 0% and 100%, adjust windowing of the image 22, select/deselect components, annotate the components, and/or include/remove components from the 3D model 40. These interactions are described in more detail in the following description.

Figure 2:
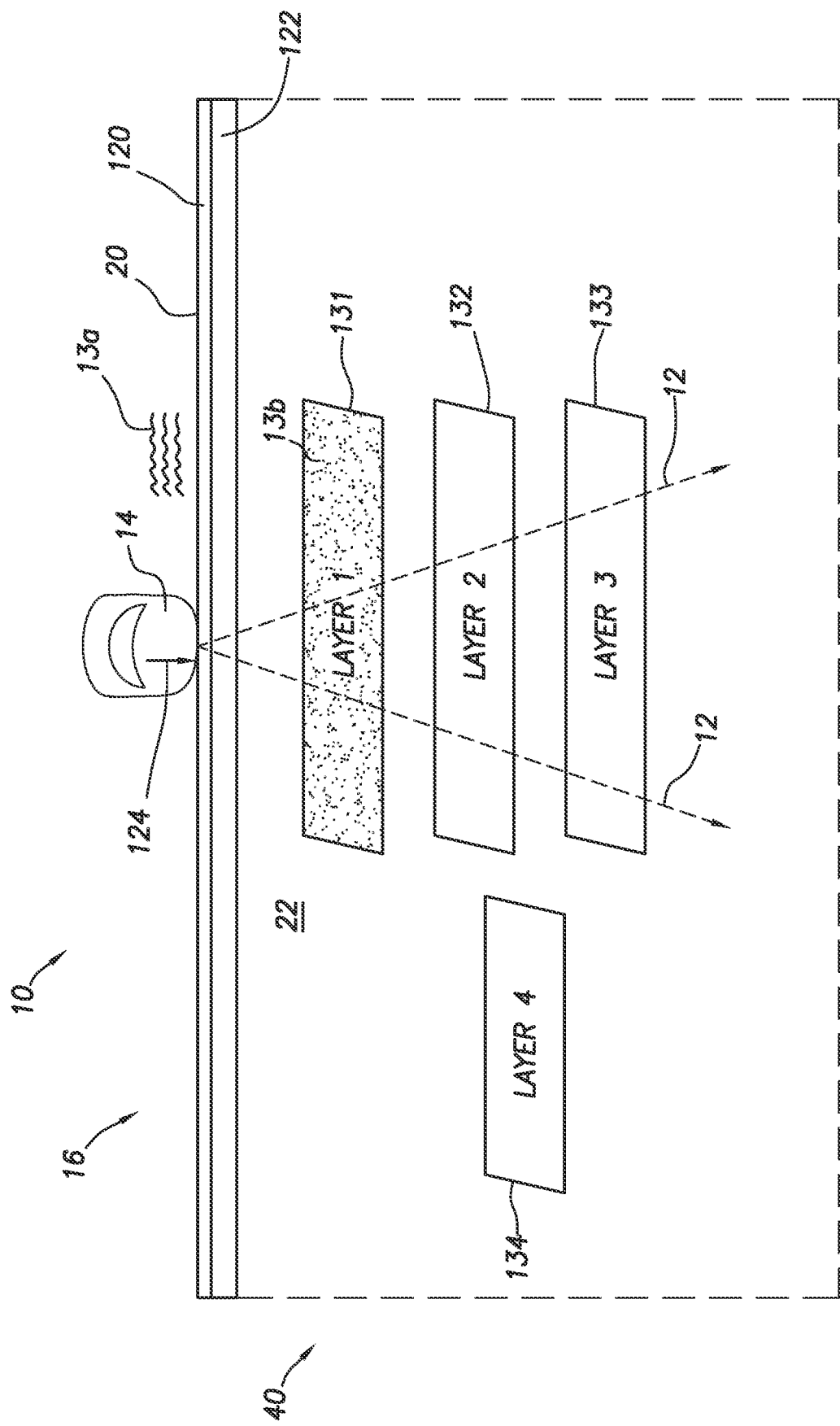
FIGS. 2-6 are representative block diagrams of a user interacting with the touchscreen of the visualization device to selectively view one or more components of an object according to some embodiments.

FIGS. 2-8 illustrate representative block diagrams of a user interface that can provide interaction between a user and various components of a 3D model 40. FIG. 2 shows a selection tool 14 (e.g. a user's finger or thumb, but can also be a stylus, a pointer, etc.) used by the user to communicate interaction commands to the computing device 16, thereby interacting with the image 22 of the 3D model 40. The visualization tool 10 can include a touchscreen 20 used to display the image 22 to the user. The touchscreen 20 can include a screen support 122, such as a glass plate, that supports a sensor layer 120. The sensor layer 120 can detect user inputs, such as pressure based inputs and/or contact based inputs, and transmit these inputs to the computing device 16 for processing. Optionally, a stereo camera 24 (see FIGS. 7 and 8) can be used to detect gesture based inputs from a selection tool 14 held above the touchscreen 20 and transmit these inputs to the computing device 16 for processing.

To illustrate various interactions between a user and the 3D model 40, four components 131-134 (indicated as layers 131-134) of the 3D model 40 are shown at various virtual positions and orientations as viewed at the touchscreen 20 from a point of view of a user. It should be understood that fewer or more components than the four components 131-134 shown in these figures can be included in the 3D model. The user's point of view is illustrated by the fixed-size viewport 12. This viewport 12 can be manipulated by the aforementioned user inputs to select, view, highlight, zoom, position, or otherwise interact with the 3D model 40. In FIG. 2, the selection tool 14 has made an initial input using the touchscreen 20. This initial input can be contact based, where the sensor layer 120 detects an electrical based (e.g. capacitive, resistive, and/or inductive) input to the visualization tool 10. This initial input can be pressure based, where the sensor layer 120 detects a pressure applied to the sensor layer 120. This initial input can select component (or layer) 131. The visualization tool 10 can indicate the selection of the component 131 via a visual response 13b (such as highlighting, temporarily moving the component 131, etc.) and/or a haptic response 13a (such as creating a vibration to indicate the selection). These components 131-134 can be partially transparent (i.e. less than 100% transparent).

The user can navigate through the 3D model 40 by various means. For example, if the initial input is detected, the user may maintain the first input for an extended time period, which can cause the visualization tool 10 to begin navigating to additional components 132-134 after the initial selection of the component 131. Therefore, an extended period of electrical contact by the selection tool 14 to the touchscreen 20, may initiate the navigation. Additionally, or in the alternative, an extended period of a pressure based contact by the selection tool 14 against the touchscreen 20 can also initiate the navigation, without requiring increased pressure to navigate to additional components of the 3D model 40. The pressure based contact can be detected by a strain gage or other suitable pressure sensors. The electrical based contact can be detected by a capacitive sensor, a resistive sensor, an inductive sensor, etc. that can detect changes in the electrical characteristics of the touchscreen 10 at the contact point of the selection tool 14. As the user navigates through the 3D model 40, the transparency of these components 131-134 can be individually adjusted to allow the user to better view the individual components in more detail. Alternatively other aspects of the component may be adjusted after the component is selected. For example the selected component may be annotated, changed in color, or otherwise visually altered.

The user may wish to probe deeper into the 3D model 40 and select other components, such as components 132-134. To select the component 132, the user may hold the selection tool 14 in contact with sensor layer 120 for an extended period of time. The extended period of time can command the visualization tool 10 to navigate to deeper components 132-134, if selection of one of the other components is desired. In one embodiment, the desired component 132-134 can be selected when the contact based input is removed (i.e. removing the selection tool 14 from contact with the sensor layer 120).

Yet another way to select other components past the initially selected component (in this example component 131) is to apply a contact pressure 124 to the sensor layer 120 of the touchscreen 20. The initial pressure based input used to select the first component 131, can be increased to indicate that navigation to another component is desired. Increasing the contact pressure 124 can command the visualization tool 10 to deselect the first component 131 and navigate to deeper and deeper components (e.g. components 132-134) as long as the increased contact pressure is applied. To select a deeper component 132-134, when the visualization tool 10 navigates to the desired deeper component 132-134, the user can decrease the contact pressure 124 thereby indicating the desired component 132-134 has been reached. The visualization tool 10 can select the desired component 132-134 in response to the decreased contact pressure 124 and provide a visual signal 13b and/or a haptic signal 13a to the user indicating that a component has been selected.

Figure 3:
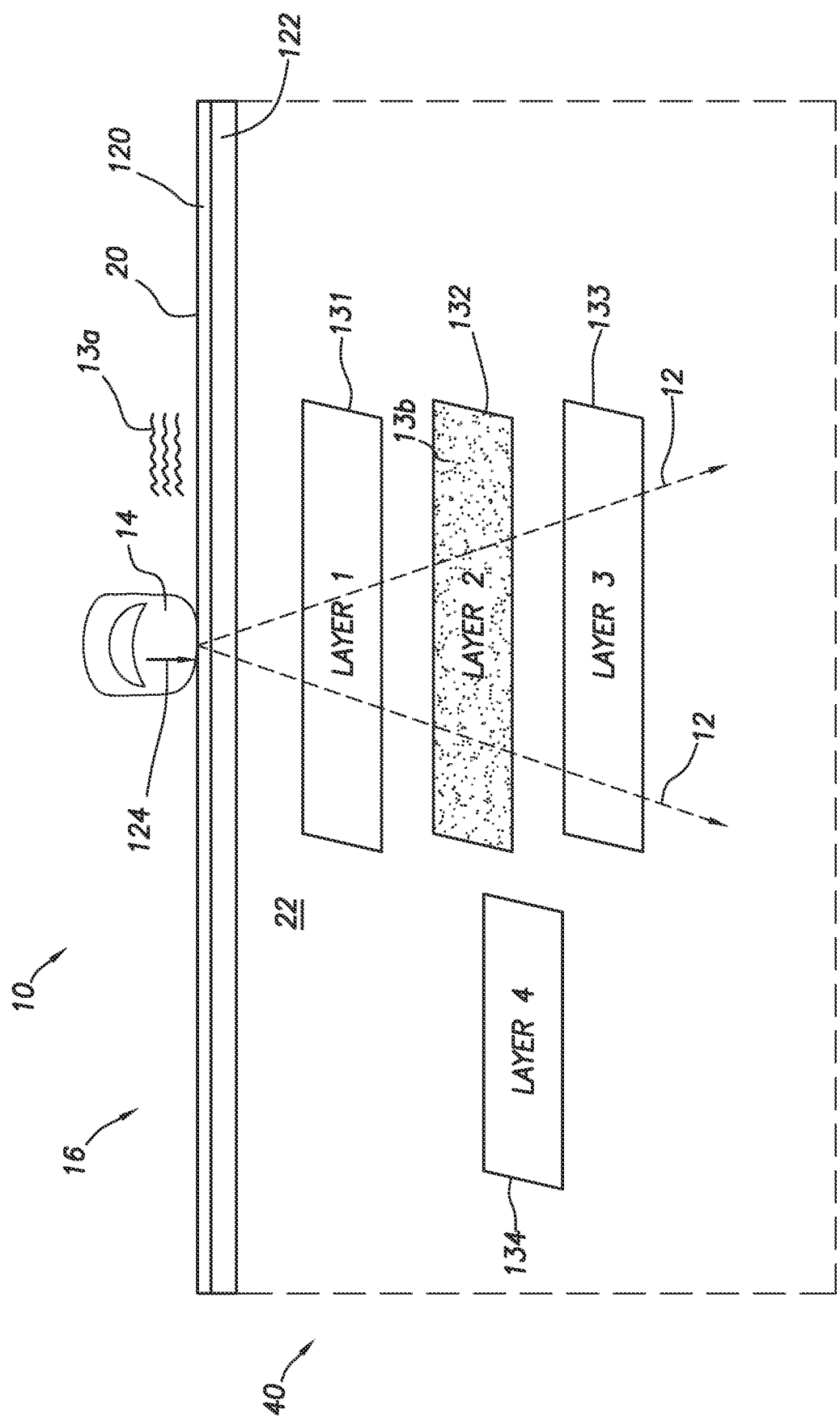

If the user desires to select an even deeper component, then the user can again increase the contact pressure 124 which will cause the visualization tool 10 to navigate to other components. As used herein, "deeper" refers to a farther distance in the virtual 3D model from the surface of the touchscreen 20. As seen in FIG. 3, an increased contact pressure 124 has been applied to the sensor layer 120 causing the visualization tool 10 to de-select component 131 and then select component 132, due to a decrease in the contact pressure 124 when the component 132 was reached. In various other embodiments, the advancement from the component 131 to the component 132 may be based on an elapsed duration of time that a contact based input is applied to the sensor layer 120. After a predetermined duration of time that the contact based input is applied to the sensor layer 120, the visualization tool 10 navigates from the component 131 to the component 132. Removing the contact based input when the component 132 is reached indicates the desired component has been reached. The visualization tool 10 may provide a visual signal 13b and/or a haptic signal 13a to the user indicating that a component 132 has been selected.

Figure 4:
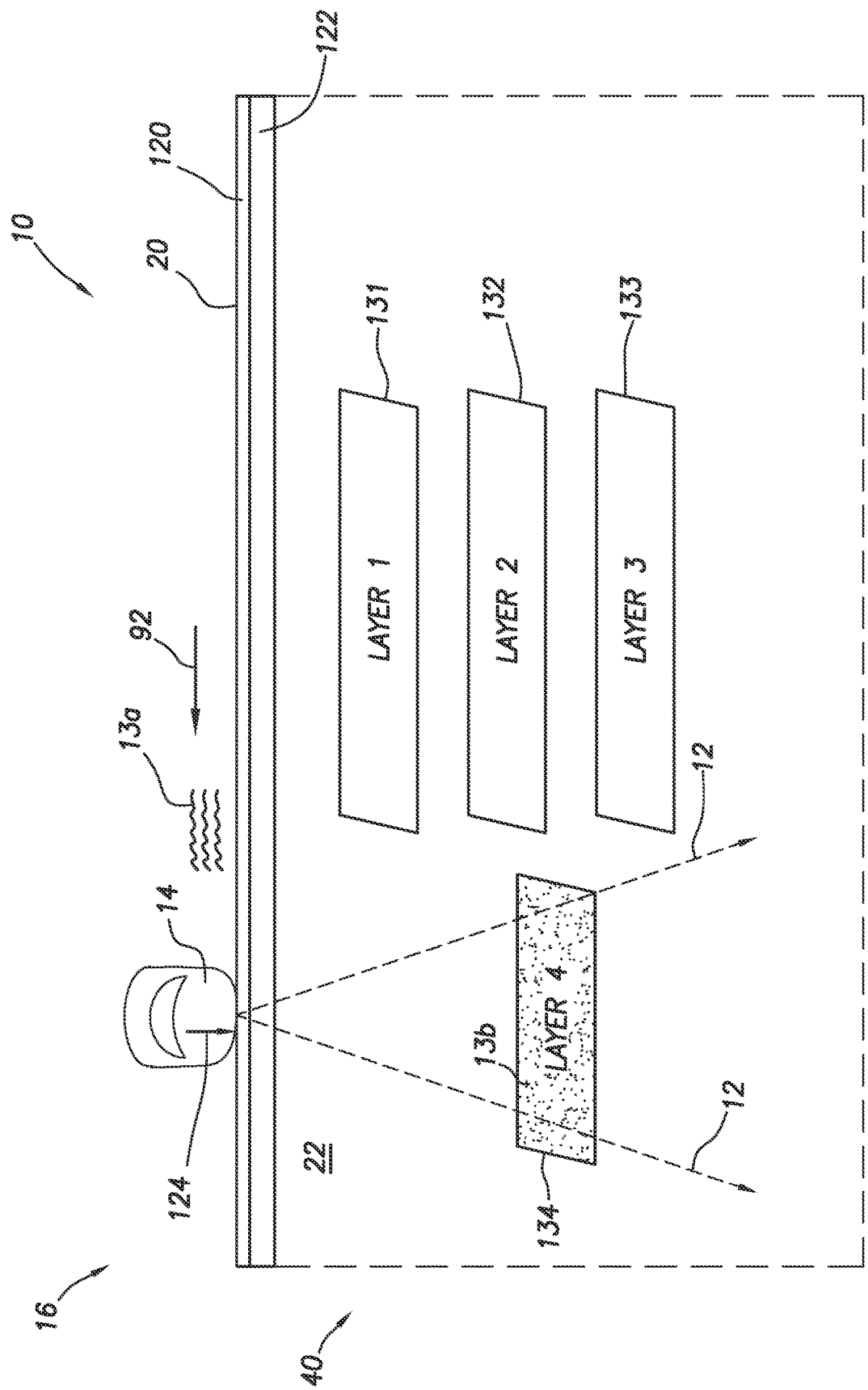

If the desired component is outside of the current fixed size viewport 12, then the user can interact with the touchscreen 20 (e.g. the sensor layer 120) to navigate to the desired component. As seen in FIGS. 2 and 3, the component 134 is shown to be outside the current fixed size viewport 12. This indicates that the component 134 is not yet visible to the user in the image 22 of the 3D model 40. FIG. 4 illustrates an example of a technique for making the component 134 visible to the user. The selection tool 14 may be moved, for example using a sliding movement 92, across the touchscreen 20. The visualization tool 10 may track the movement 92 of the selection tool 14 with a corresponding matching movement of the fixed size viewport 12. Moving the fixed size viewport 12 to position on the touchscreen 20 over the component 134 can allow the selection tool 14 to select component 134 in the various ways described above for selecting a component with contact based and/or pressure based inputs.

Figure 5:
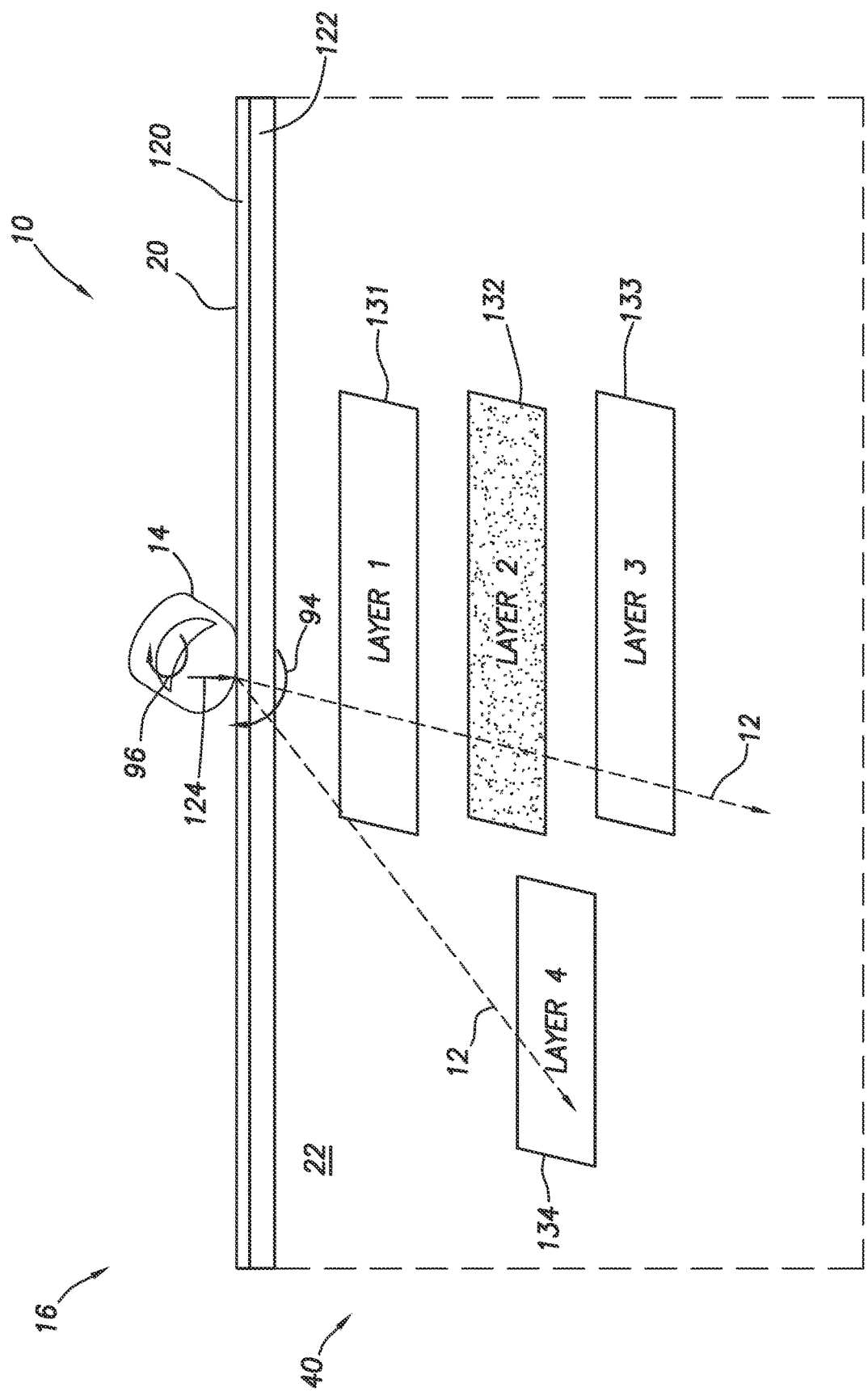
Figure 6:
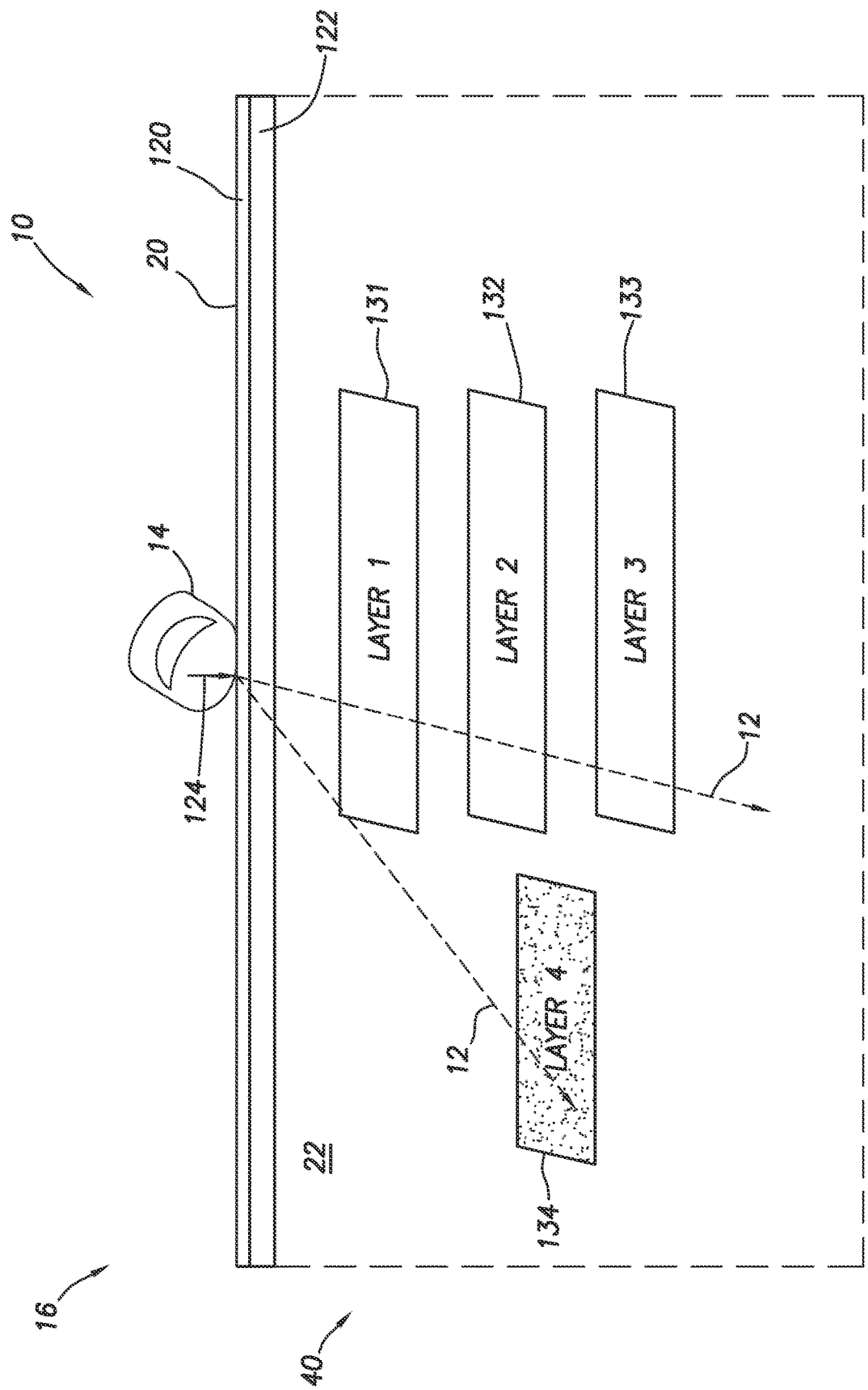

FIG. 5 illustrates another example of a technique for making the component 134 visible to the user. This example may be used with or without sliding the selection tool 14 across the touchscreen 20 as described in FIG. 4. In this example, a rotational motion 96 of the selection tool 14 can result in a rotational motion 94 of the fixed size viewport 12. The motion of the fixed size viewport 12 is similar to having a cone shaped viewing frame extending from the selection tool 14 at the surface of the touchscreen 20. As the selection tool 14 is rotated on the sensor layer 120, the fixed size viewport 12 tracks the rotation of the selection tool 14 as if it were rotationally locked to the selection tool 14. It should be understood that the sliding movement 92 in FIG. 4 can be combined with the rotational movement 96 of FIG. 5 to assist the user in navigating to various components in the 3D model 40. FIG. 6 indicates that the component 134 has been selected after rotation of the fixed size viewport 12. As previously described, the selection of the component 134 can be performed by a contact based input and/or a pressure based input. Again the selection of the component 134 can indicated by a visual signal 13b and/or a haptic signal 13a produced by the visualization tool 10.

Figure 7:
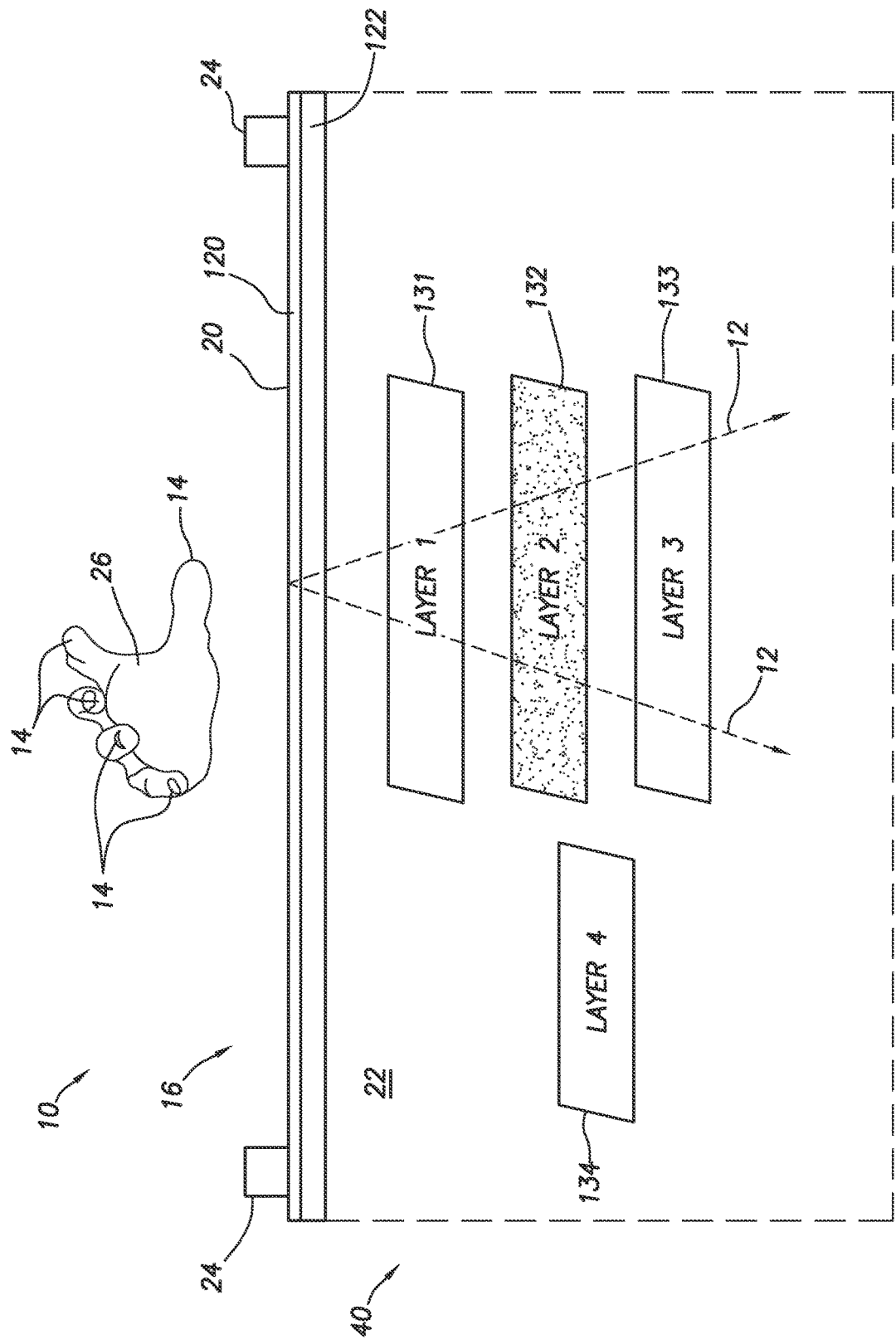
FIGS. 7-8 are representative block diagrams of a user interacting with the touchscreen of the visualization device with a stereo camera to selectively view one or more layers and/or components of the object according to some embodiments.

FIG. 7 illustrates a visualization tool 10 with a computing device 16, a touchscreen 20, and a stereo camera 24 for interacting with an image 22 of the 3D model 40. The stereo camera 24 can detect gestures of the selection tools 14 and 26. Selection tools 14 and 26 are shown as human digits and a human hand, respectively. However, other selection tools (e.g., wands, gloves) can be used to communicate predetermined gestures to the visualization tool 10 via the stereo camera 24 or other visual or motion sensors. As shown in FIG. 7, component 132 has been selected and a visual signal 13b and/or a haptic signal 13a has been produced by the visualization tool 10 to indicate the selection (similar to FIG. 3). A predetermined gesture of the selection tools 14 and/or 26 can cause the visualization tool 10 to travel through the components 131-134 in the 3D model 40, with a second predetermined gesture of the selection tools 14 and/or 26 used to indicate the desired component has been reached (component 132 in this example) and that the user desires to select the desired component 132. A visual signal 13b and/or a haptic signal 13a can be produced by the visualization tool 10 to indicate the selection of the component 132.

Figure 8:
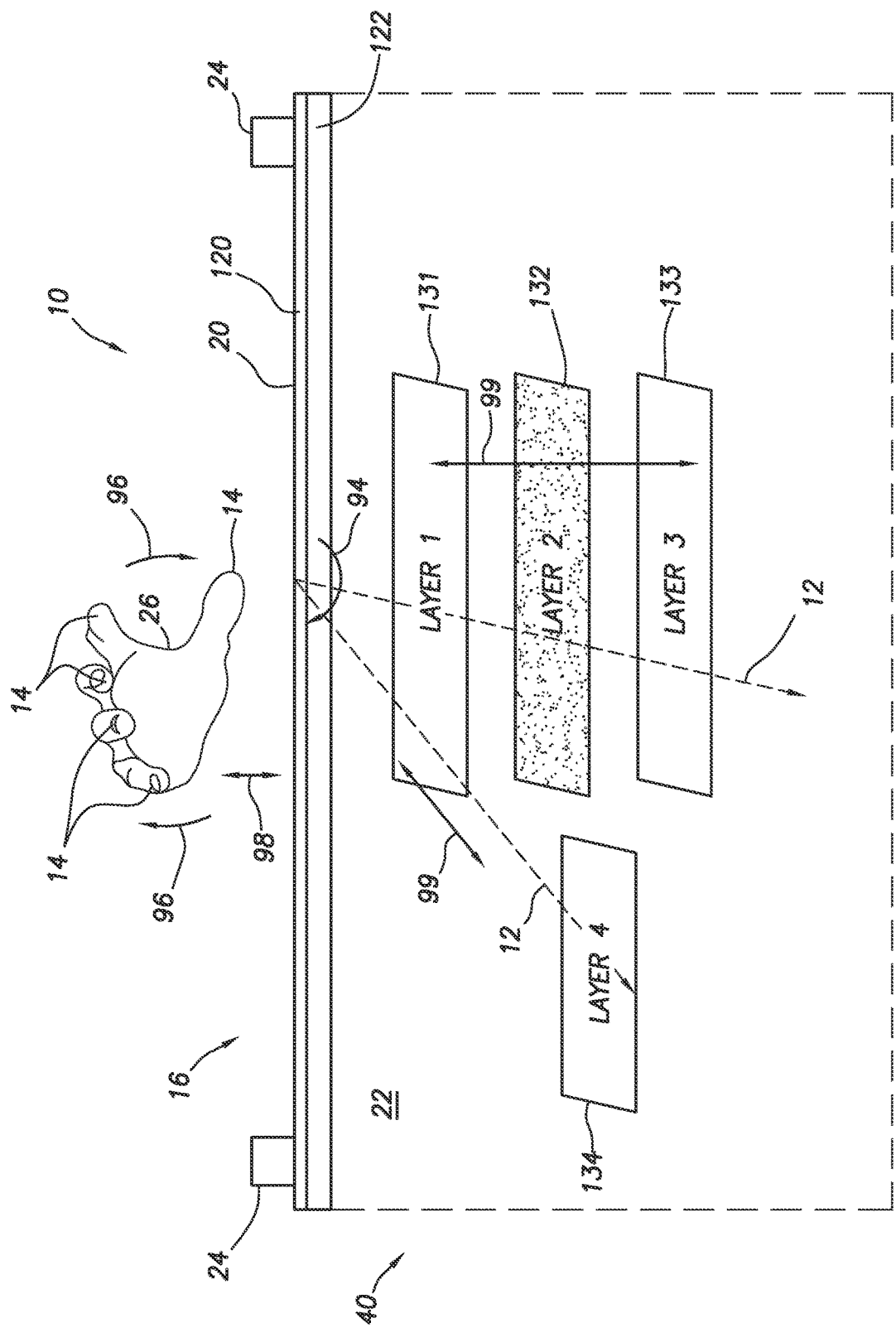

FIG. 8 illustrates an embodiment in which the selection tool may be rotated (movement 96) to cause the fixed size viewport 12 to be rotated (movement 94) and allow viewing of components that visible in the initial fixed size viewport 12 (similar to FIGS. 5 and 6). While the rotational gesture (movement 96) can cause the fixed size viewport 12 to rotate (movement 94), other predetermined gestures (such as moving selection tools 14 and/or 26 toward and/or away from the touchscreen (movement 98) can be used to navigate to deeper and shallower components (movement 99). Many other predetermined gestures (not shown) can be defined for zooming the image 22, focusing the image 22, adjusting brightness of the image 22, adjusting transparency of the various components 131-134, etc. Gestures may also be used to measure the size of an object. For example, a user thumb and index finger may hover at a predefined distance range above the device 16. Detection of the pose of the thumb and index finger (and/or other portions of the hand) may launch a measurement tool that scales to the distance between the thumb and index finger such that the distance can be used to measure the size of objects bounded by the thumb and index finger distance. Other hand poses may be mapped to different functions and dimensions.

Referring again to FIGS. 2-8, once the desired component 131-134 has been selected, other user inputs can be detected to adjust a display parameter of the component 131-134. The adjustable display parameter can be transparency, windowing, zoom image in, zoom image out, brightness, contrast to other components, grouping/ungrouping multiple components, image position, and other suitable display parameters that can beneficially be adjusted.

Figure 9:
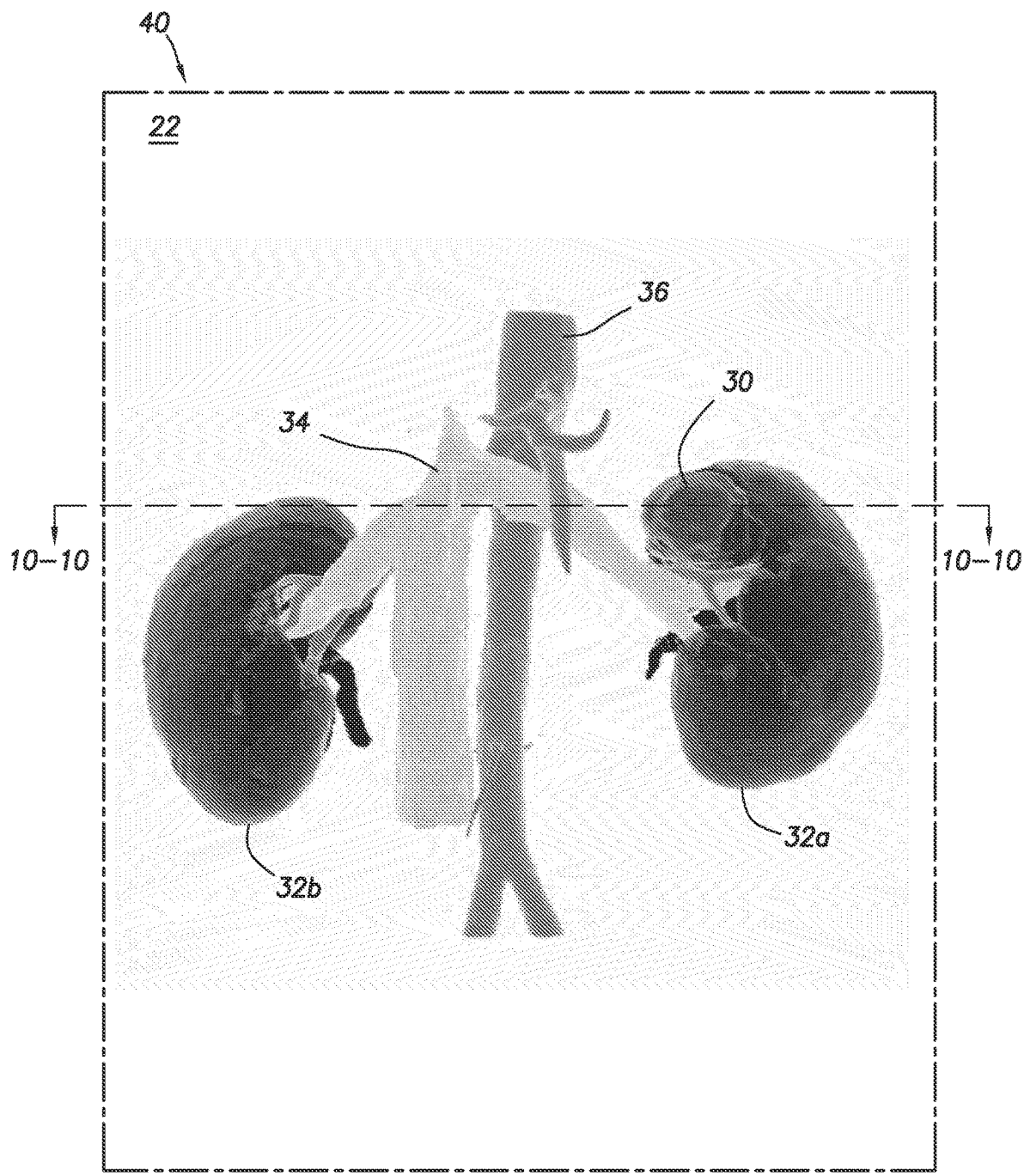
FIG. 9 is a representative perspective view of an image of a 3D model displayed a touchscreen according to some embodiments.
Figure 10:
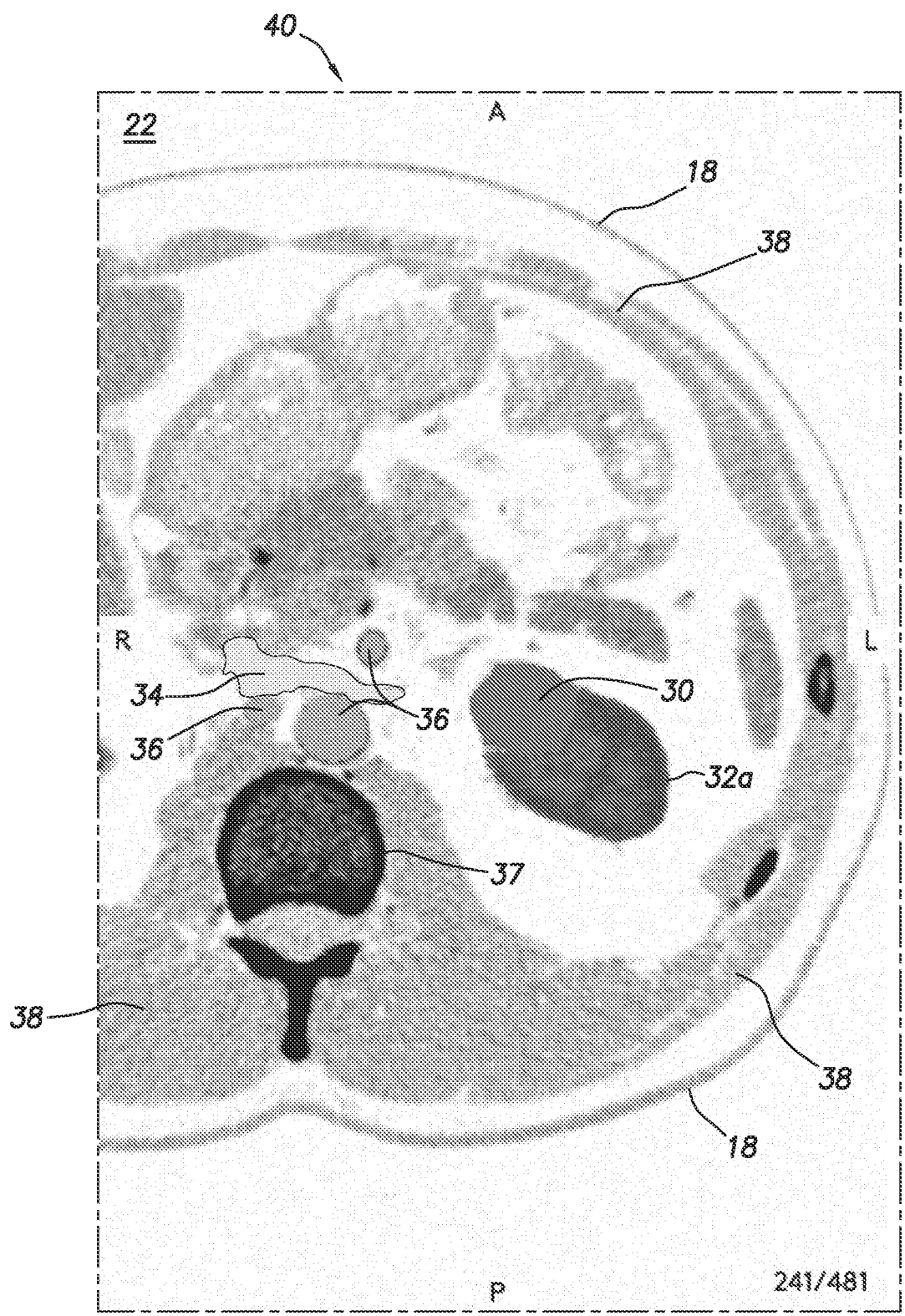
FIG. 10 is a representative view of components of a 3D model (in this example, a cross-sectional view of the 3D model built from a CT scan) as seen on a touchscreen user interface according to some embodiments.

FIG. 9 illustrates a representative perspective view of components 30, 32*a*, 32*b*, 34, 36 of a 3D model 40 that may be displayed as the image 22 via the visualization tool 10. In this example, the components are virtual 3D renderings of anatomic objects or systems which include a tumor 30, a left kidney 30*a*, a right kidney 30*b*, a vein 34, and an artery 36. It should be understood more or fewer components can be included in the image 22. The number of components, as well as the particular components, of the model 40 is provided here for illustration purposes only. These components 30, 32*a*, 32*b*, 34, 36 can represent a subset of components of the object, where the other components in the object are transparent in the image 22. Therefore, only a subset of components of the patient anatomy may be visible in the image 22.

Referring to FIGS. 10-13B, these figures can represent a cross-sectional view of the 3D model 40 indicated as view 10-10 in FIG. 9. This cross-sectional view may be, for example, a layer of a CT or MR image scan that has been rendered as the 3D model 40. The cross-sectional view 10-10 shown in FIG. 10 includes image data at that location of the 3D model 40 in addition to a cross-sectional portion of each of the components 30, 32*a*, 32*b*, 34, 36 at a corresponding location of the 3D model 40. The portions of the components 30, 32*a*, 32*b*, 34, 36 are shown along with cross-sectional views of the skin 18, other surrounding tissue 38, and spine 37 at the corresponding location.

It should also be understood that FIGS. 10-13B are shown as negative views of the actual user interface images 22 to allow better clarity, since the background color of the images 22 are actually black and the images with the black background made figures less clear than was desirable. Therefore, it should be understood, that the darker items in the images are actually the lighter items and the lighter items in the images 22 are actually the darker items when the images 22 are viewed on the actual touchscreen 20 of the visualization tool 10.

Figure 11A:
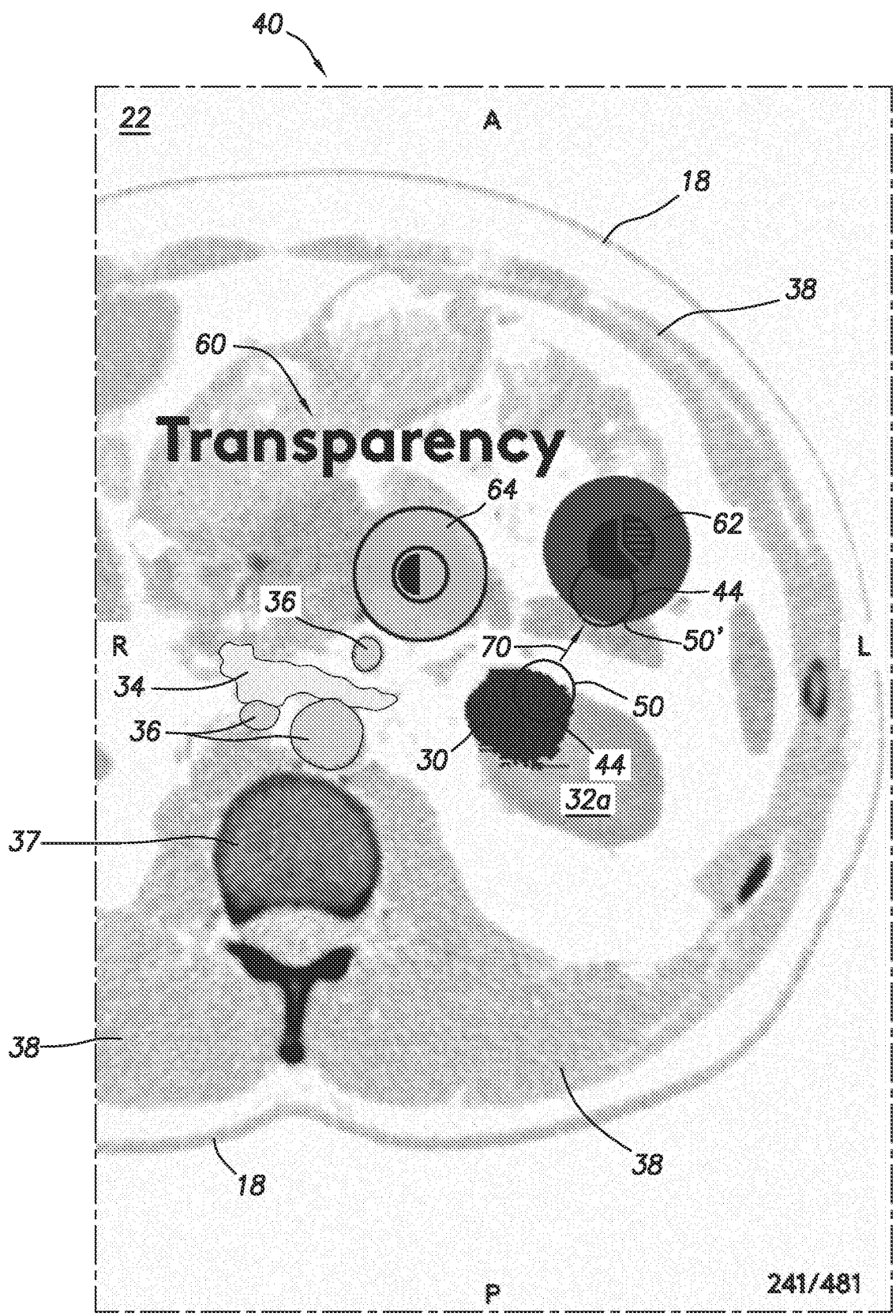
FIGS. 11A-11B are representative views of the touchscreen user interface interacting with the components of FIG. 10 to adjust a transparency of one of the components according to some embodiments.
Figure 11B:
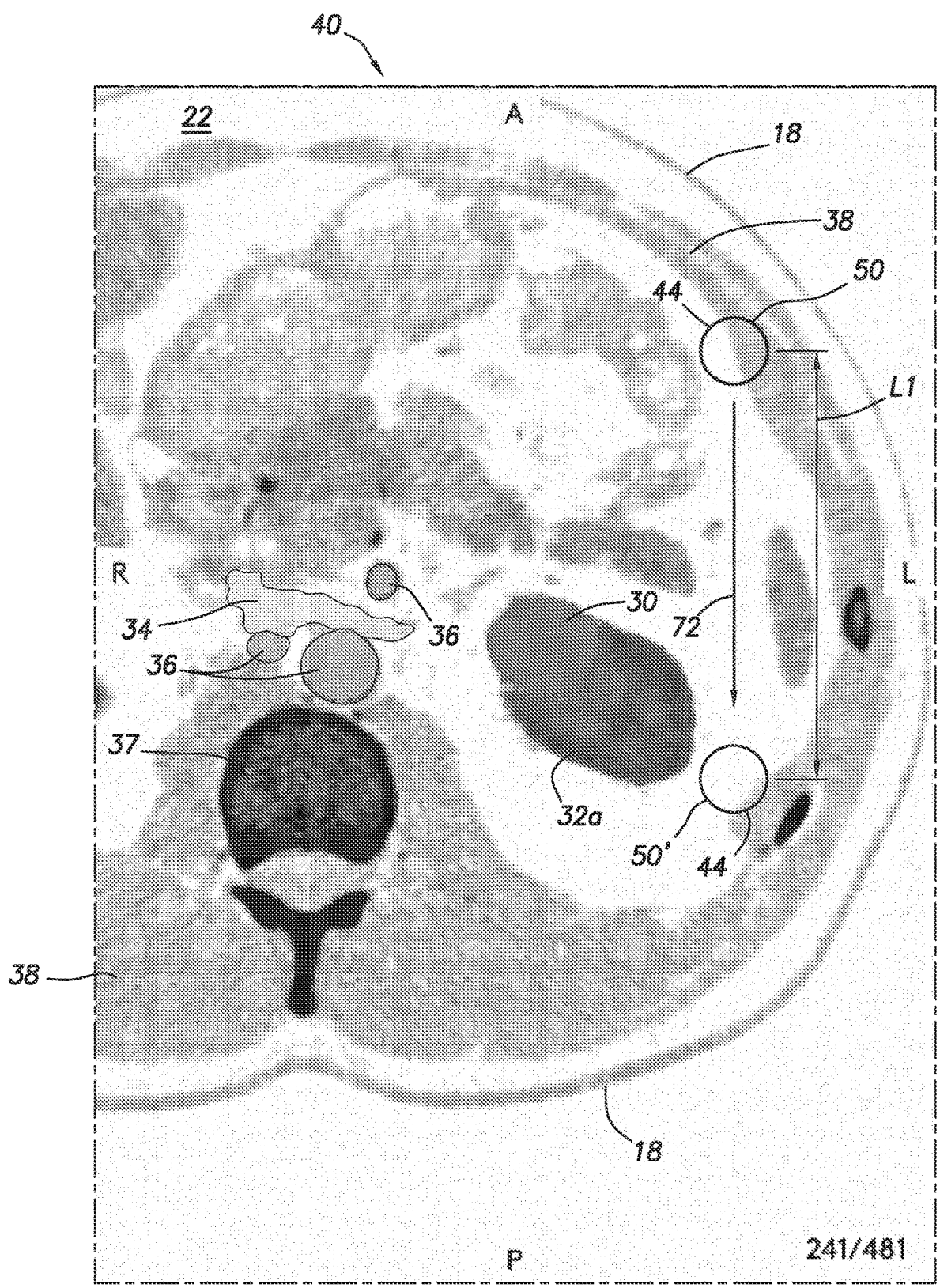

FIGS. 11A-11B illustrate how the visualization tool 10 may be used to adjust a display parameter of the components 30, 32*a*, 32*b*, 34, 36 via the user interface of the visualization tool 10. If it is desired to change a transparency display parameter, then a first input (e.g., contact based, pressure based, or gesture based) can be applied to the touchscreen at a location 50 which is above the desired component to be selected. The input is detected by the touchscreen, and the location 50 of the first input is indicated on the touchscreen 20 by an icon 44 displayed at location 50. In this example the icon 44 is a ring icon. However, the icon 44 can be any number of other shapes and sizes in keeping with the principles of this disclosure, such as triangle, oval, star, square, polygon, etc. Detecting the location 50 of the input can cause the computing device 16 to select the component 30 and provide a visual signal 13*b* and/or a haptic signal 13*a* to the user to indicate that the component 30 has been selected. Once the computing device 16 detects the input and selects the component 30, the computing device 16 can display two selectable icons 62, 64. These icons 62, 64 may be visually different from each other to aid the user in selecting the desired icon 62, 64. These selectable icons 62, 64 can be used to select which adjustable parameter (e.g. transparency, windowing) the user desires to adjust with the visualization tool 10. More than two selectable icons can be provided, if desired.

The first input can be used to move the icon 44 (movement 70) across the touchscreen 20 from the location 50 to the location 50' to select icon 62. When the icon 44 at least partially overlaps the selectable icon 62, the computing device 16 can indicate that the icon 62 is selected by providing the user with a visual and/or haptic signal when the selection occurs. With the icon 62 selected, the computing device 16 can display text 60 on the touchscreen (such as "TRANSPARENCY") to indicate which display parameter has been selected.

Referring now to FIG. 11B, with the transparency display parameter selected and the desired component (for example component 30) selected, the user can then adjust the transparency display parameter by providing a second input at the touchscreen 20 at location 50 with the computing device indicating that the input has been detected by displaying the icon 44 at the location 50. Moving the second input (i.e. movement 72) along the touchscreen 20 to the location 50' can adjust the transparency of the selected component (e.g. component 30) by either increasing or decreasing a percentage of transparency within an inclusive range from 0% to 100%. FIG. 11B indicates that the movement 72 of the input across the touchscreen 20 increases the transparency of the selected component. Movement in an opposite direction relative to movement 72 can cause a decrease in the transparency of the selected component. However, it should be understood that the computing device 16 can be programmed such that the movement 72 of the input along the touchscreen can decreases the transparency of the selected component, with movement in an opposite direction relative to movement 72 can increase the transparency of the selected component. If the input moves a distance L1 then the transparency of the selected component can be set to the maximum (100%) or minimum (0%), depending upon whether the movement 72 is causing the transparency display parameter to increase or decrease, respectively.

Referring to FIGS. 12A-D, and 13A-B, these figures illustrate the interactions of a user with the touchscreen 20 to adjust a display parameter called "windowing." Windowing is a well-known term at least in the art of radiology imaging that generally refers to adjusting the contrast and/or brightness of surrounding tissue in a CT scan or MR scan model.

Figure 12A:
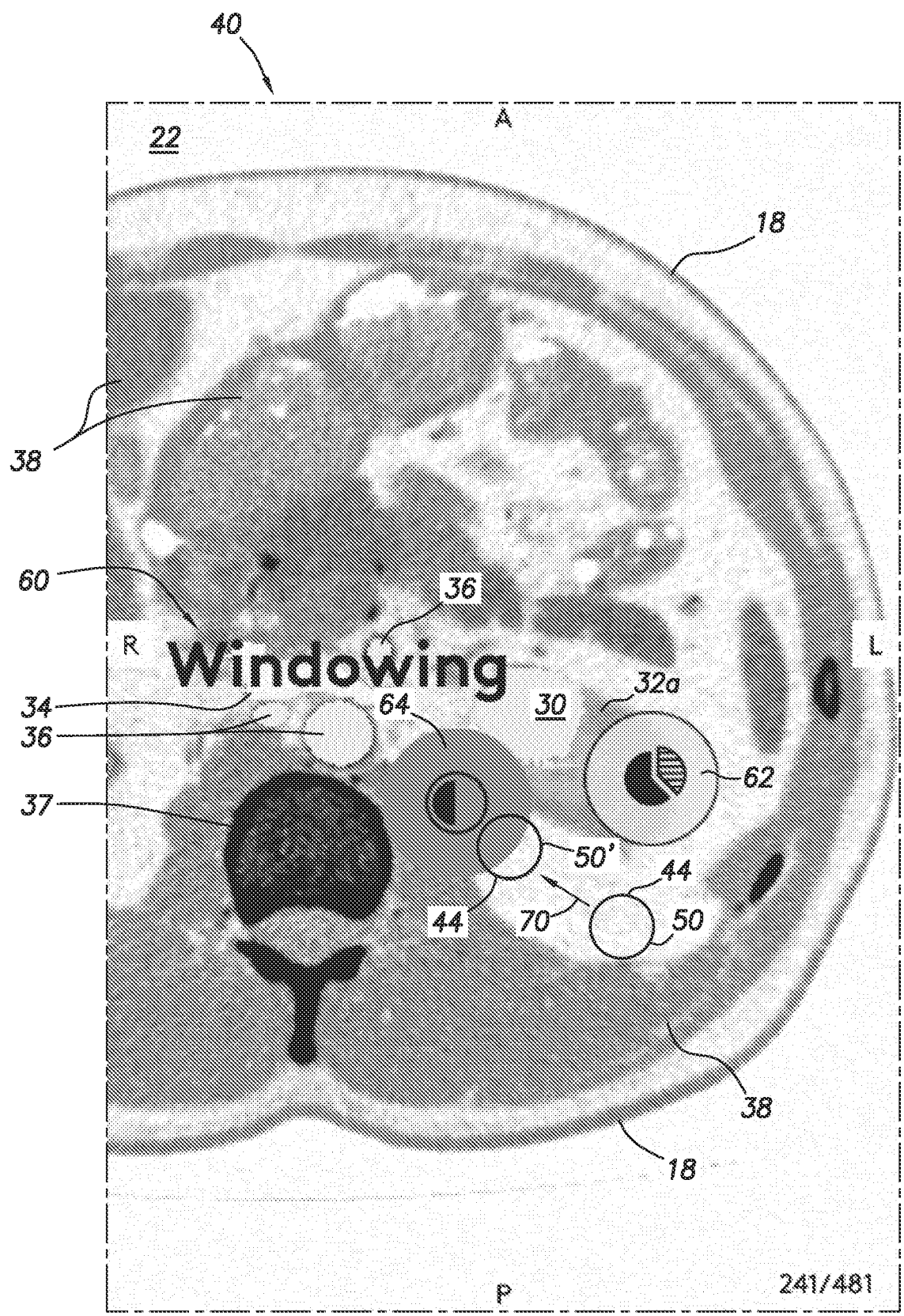
FIGS. 12A-13B are representative views of the touchscreen user interface interacting with the components of FIG. 10 to adjust a windowing of one of the components according to some embodiments.

Referring now to FIG. 12A, if it is desired to change a windowing display parameter, then a first input (contact based or pressure based) can be applied to the touchscreen at a location 50 which is above a desired component to be selected. The input is detected by the touchscreen, and the location 50 of the first input is indicated on the touchscreen 20 by an icon 44 displayed at location 50. Detecting the location 50 of the input can cause the computing device 16 to select the component (in this example, the surrounding tissue layer 38 is selected) and provide a visual signal 13b and/or a haptic signal 13a to the user to indicate that the component has been selected. Once the computing device 16 detects the input and selects the component 38, the computing device 16 can display two selectable icons 62, 64. These icons 62, 64 may be visually different from each other to aid the user in selecting the desired icon 62, 64. These selectable icons 62, 64 can be used to select which adjustable parameter the user desires to adjust with the visualization tool 10. More than two selectable icons can be provided, if desired.

The first input can be moved (movement 70) across the touchscreen 20 from the location 50 to the location 50' to select icon 64. When the icon 44 at least partially overlaps the selectable icon 64, the computing device 16 can indicate that the icon 64 is selected by providing the user with a visual and/or haptic signal when the selection occurs. With the icon 64 selected, the computing device 16 can display text 60 on the touchscreen (such as "WINDOWING") to indicate which display parameter has been selected.

Figure 12B:
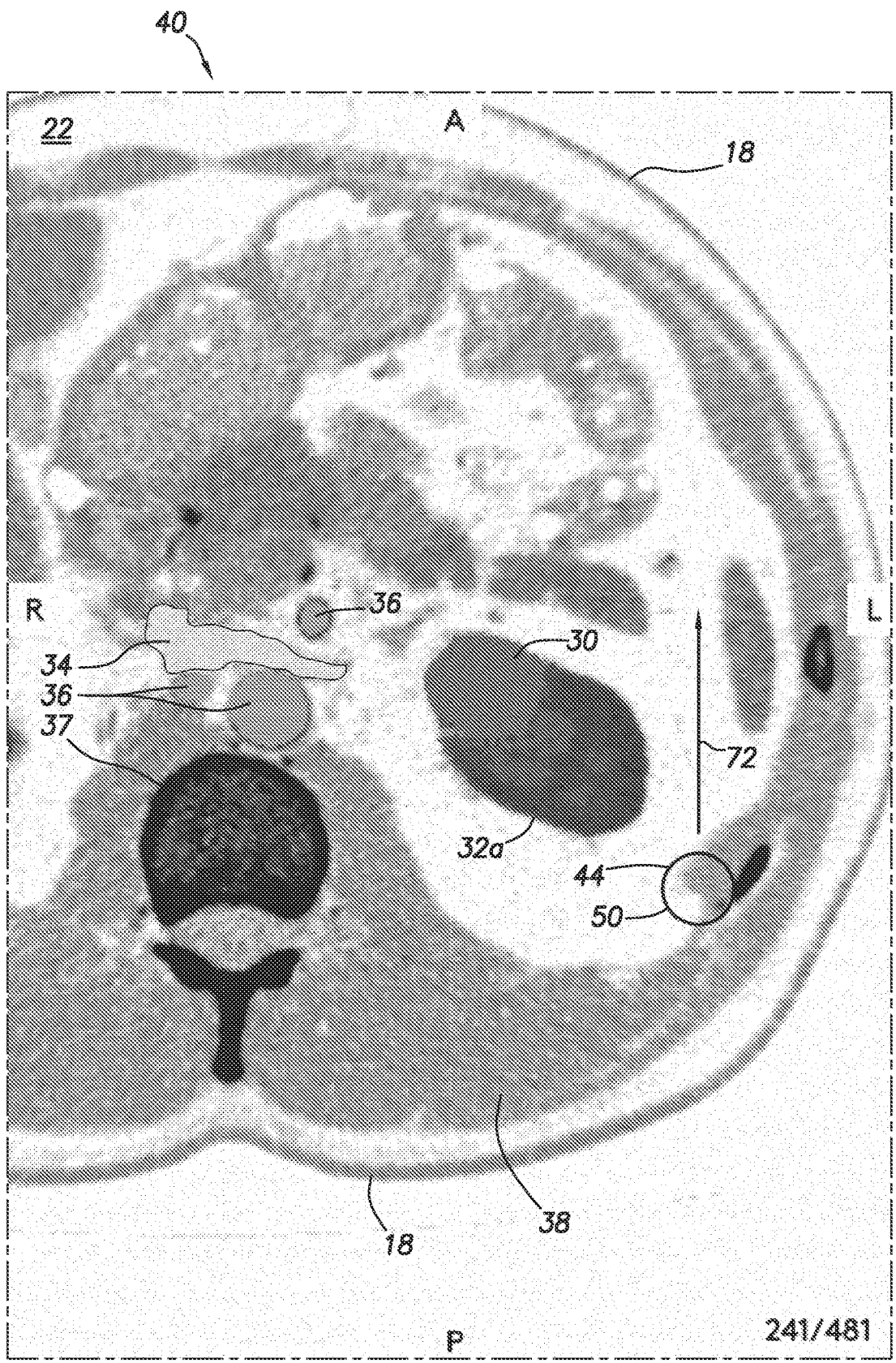
Figure 12C:
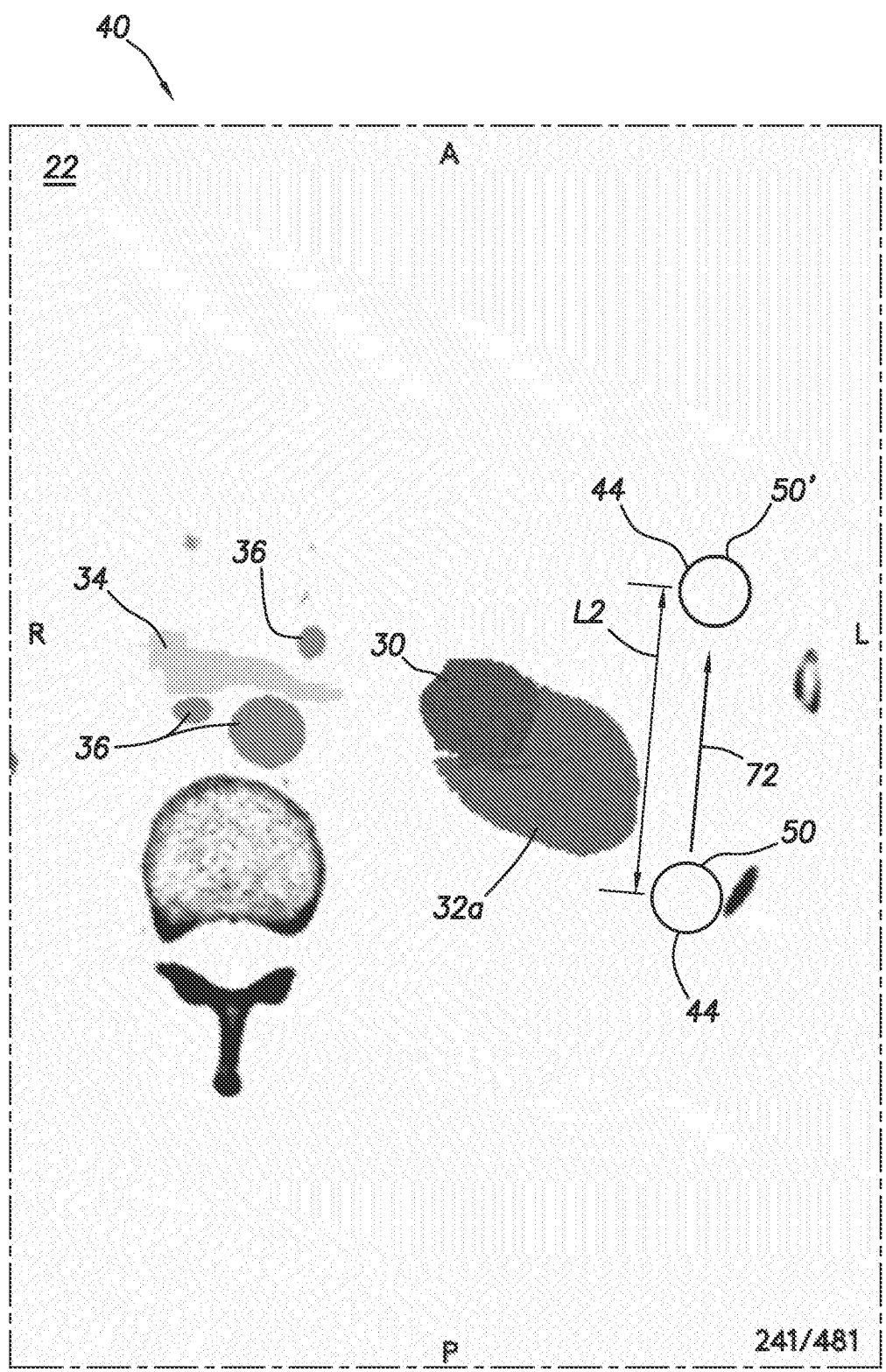

Referring now to FIGS. 12B-12C, with the windowing display parameter selected and the desired component (for example component 38) selected, the user can then adjust the display parameter by providing a second input at the touchscreen 20 at location 50 with the computing device indicating that the input has been detected by displaying the icon 44 at the location 50. Moving the second input (i.e. movement 72) along the touchscreen 20 to the location 50' can adjust the windowing of the selected component (e.g. component 38) by either decreasing or increasing the windowing to enhance the features of the component or subdue the features of the component, respectively. FIG. 12C indicates that the movement 72 of the input across the touchscreen 20 to the location 50' has increased the windowing and subdued the selected component 38 such that almost all of the features of the component (e.g. surrounding tissue, skin 18) is displayed as mostly white except for the bone portions (e.g. spine 37) which are still mostly black. Movement in an opposite direction relative to movement 72 can cause the windowing of the selected component 38 to be enhanced by returning the component to an image with defined features of the component 38 more easily visible from a "washed out" view of the increased windowing in FIG. 12. The increased windowing subdues the portions of the component 38 by decreasing a color differential between different tissues and between tissue and bone. However, it should be understood that the computing device 16 can be programmed to decrease the windowing of the selected component in response to the movement 72, and movement in an opposite direction relative to movement 72 can be programmed to increase the windowing of the selected component.

Figure 12D:
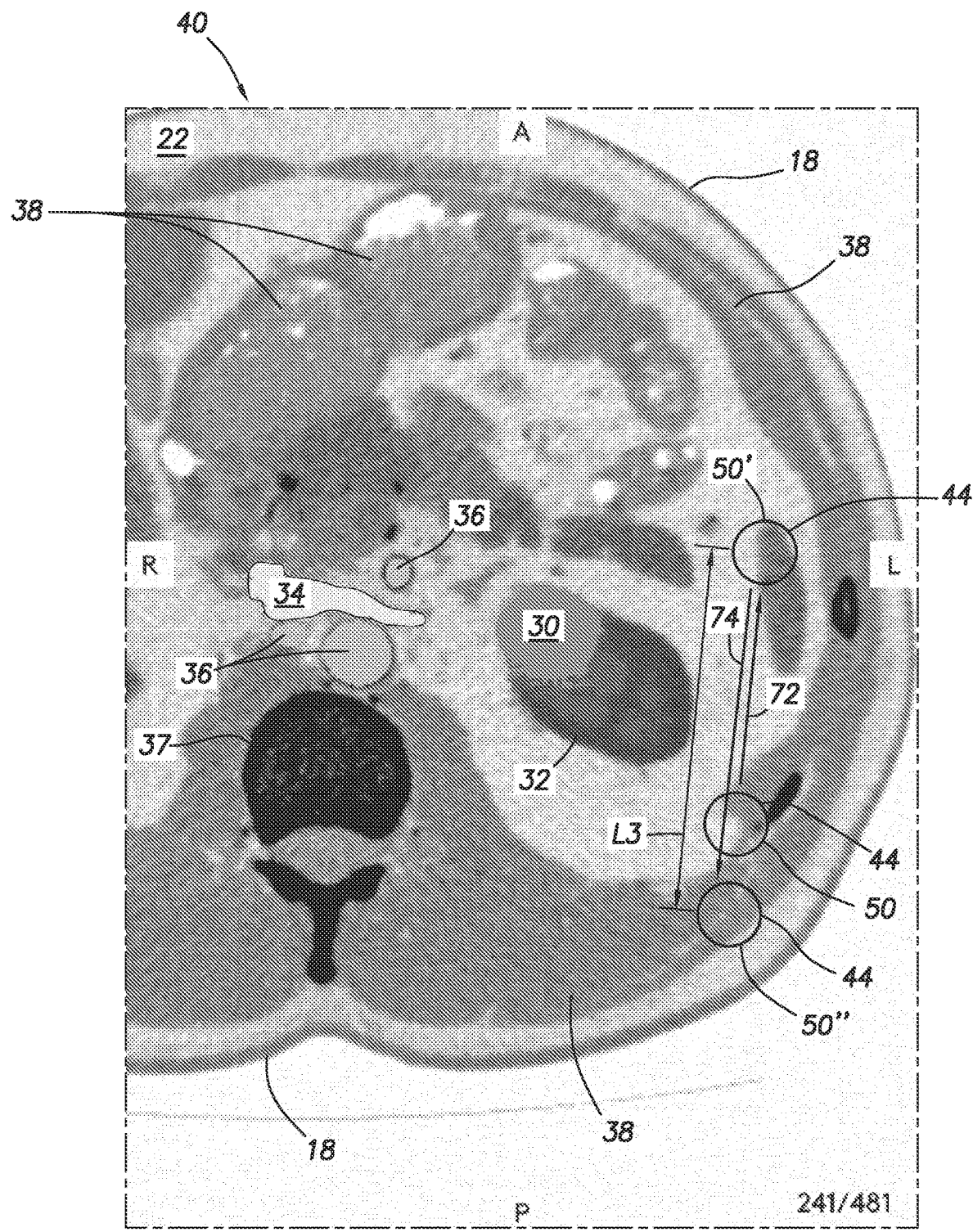

Referring to FIG. 12D, after moving the second input from location 50 to location 50', the second input can be moved (movement 74) along the touchscreen 20 to a location 50". The computing device 16 can indicate the movements of the second input by displaying the icon 44 at the location on the touchscreen 20 of the second input while the second input is contacting the touchscreen 20. In this example, the movement 74 of the second input decreases the windowing, thereby enhancing the definition of the portions of the component 38 by increasing a color differential between different tissues and between tissue and bone displayed as component 38. The distance of travel L2 of the second input from location 50 to location 50' is less than the distance of travel L3 of the second input from location 50' to location 50". Therefore, it can be seen that the initial windowing value of the component 38 is lower at location 50" than at the beginning of the adjustment when the second input was at location 50. The movement of the second input on the touchscreen 20 can continue until a maximum or minimum value of windowing is reached.

Figure 13A:
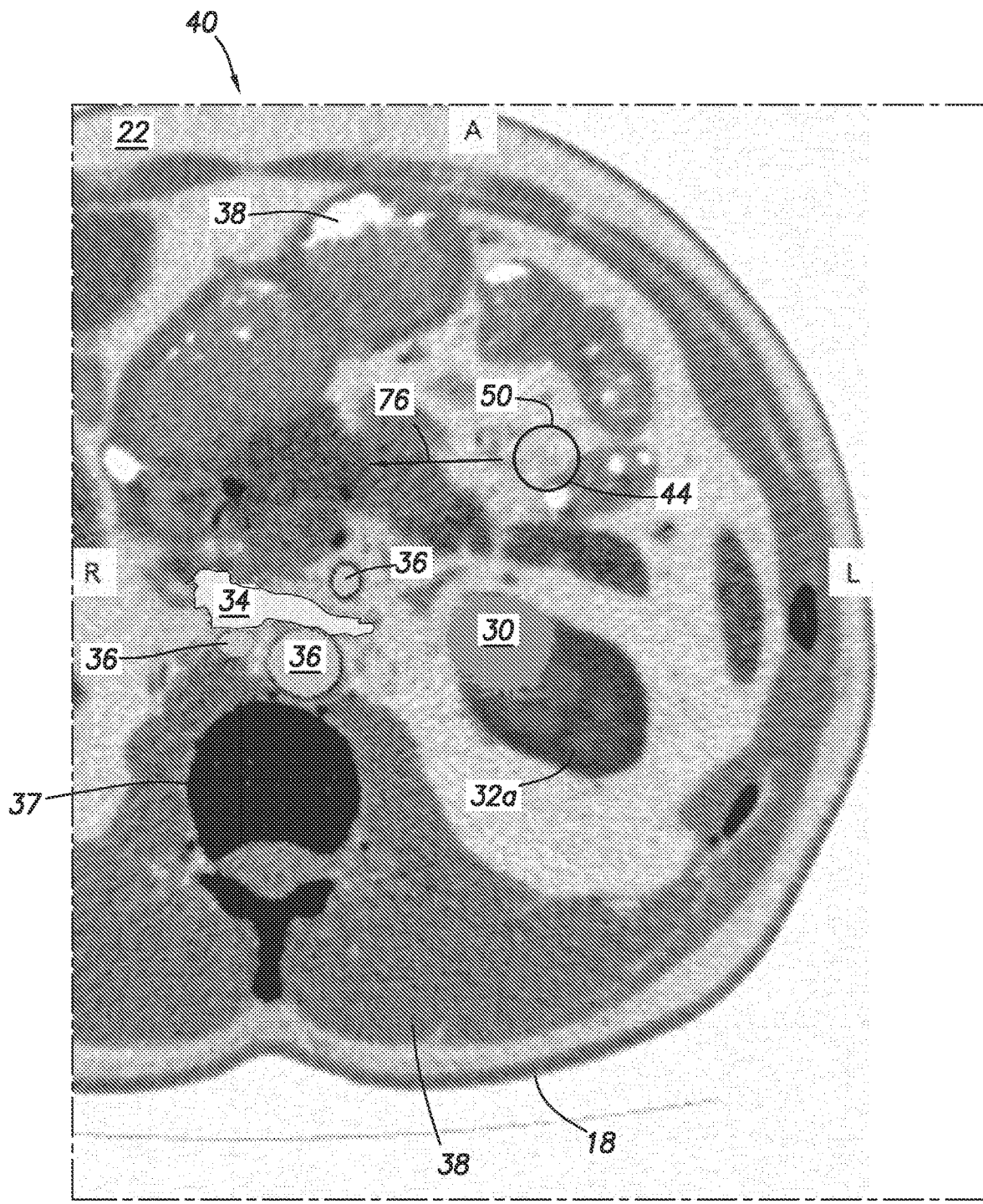
Figure 13B:
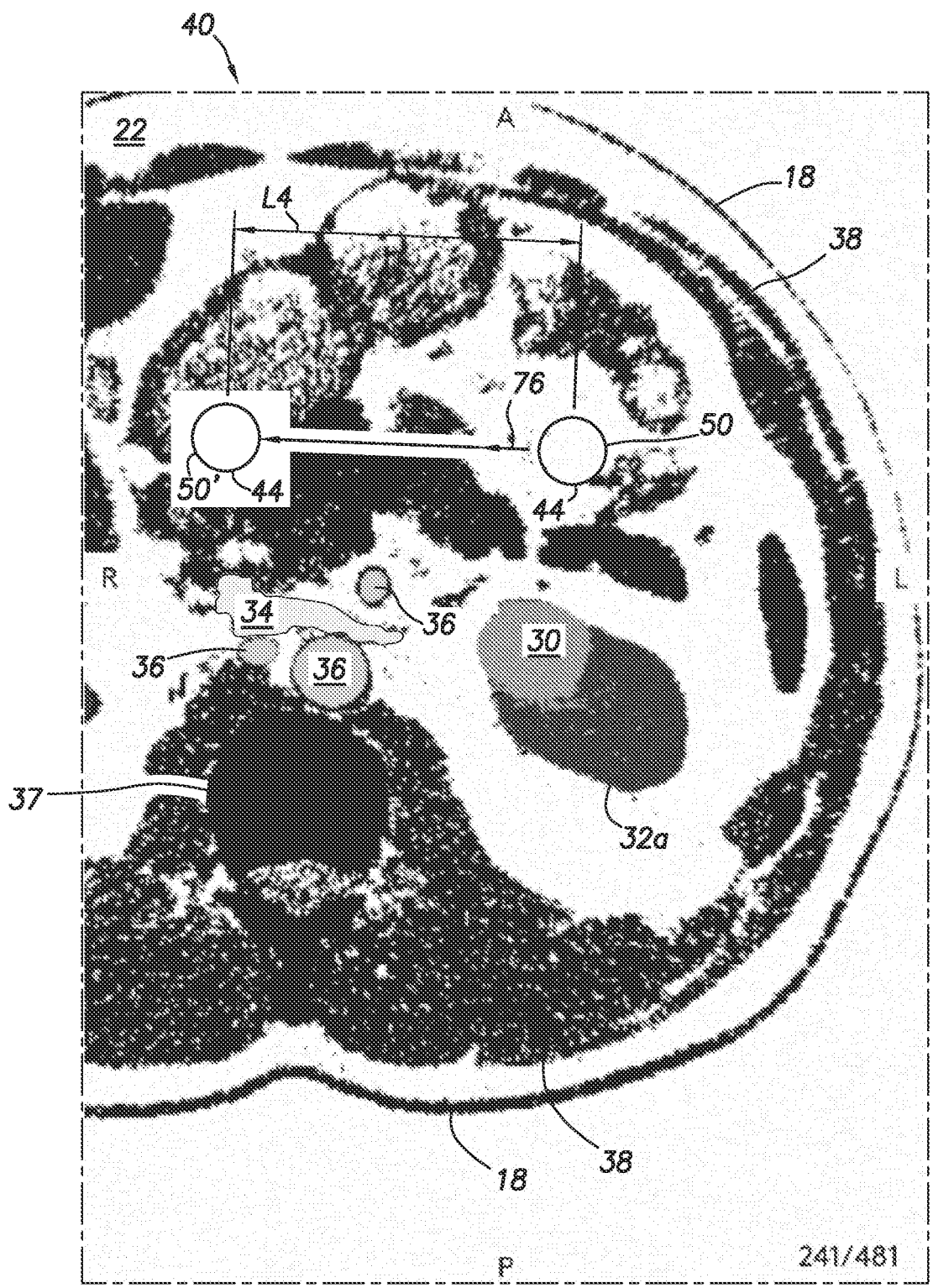

Windowing has a second aspect of adjustment, with the first aspect being described with reference to FIGS. 12A-D above. The second aspect is a type of contrast adjustment. Referring to FIGS. 13A-B, after the first input has selected the desired component (component 38 in this example) and selected windowing as the display parameter to be adjusted, the second input can be used to adjust the second aspect of the windowing display parameter. As where the movements 72, 74 are in the up and down directions (relative to the figures), the movement 76 to adjust the second aspect of the windowing parameter is in the left and right directions.

Applying a second input at the touchscreen 20 at location 50, the computing device can indicate that the input has been detected by displaying the icon 44 at the location 50. Moving the second input (i.e. movement 76) along the touchscreen 20 to the location 50' can adjust the second aspect of the windowing of the selected component (e.g. component 38) by either decreasing or increasing the second aspect to increase or decrease contrast between the features of the component. FIG. 13B indicates that the movement 76 of the input across the touchscreen 20 to the location 50' has increased the second aspect and has reduced the available levels of color in the image of component 38 (such as reducing the available levels of gray in a grayscale image). The selected component 38 is shown in FIG. 13B as having in increased the second aspect of the windowing display parameter, such that almost all of the features of the component 38 are almost either black or white, since the levels of color are restricted to only a few levels. Movement in an opposite direction relative to movement 76 can cause the second aspect of the windowing to be decreased by returning the component to an image with defined features of the component 38 more easily visible from highly contrasted view of the increased windowing in FIG. 13B. However, it should be understood that the computing device 16 can be programmed to decrease the second aspect of the windowing of the selected component in response to the movement 76, and movement in an opposite direction relative to movement 76 can be programmed to increase the second aspect of the windowing of the selected component.

Figure 14A:
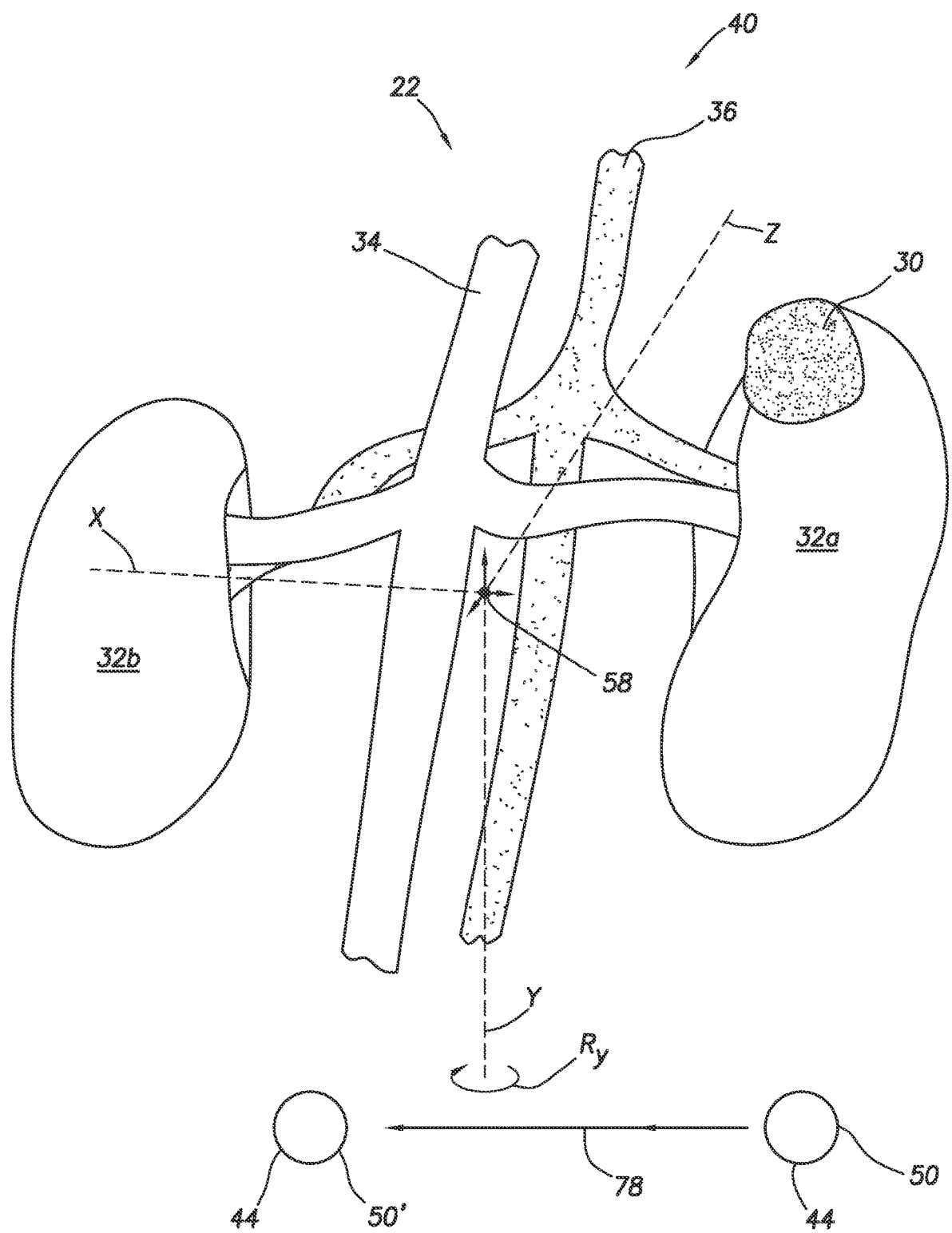
FIGS. 14A-14B are representative perspective views of components of a 3D model (in this example, a 3D rendering of human organs) as seen on a touchscreen user interface as well as interactions for revolving the 3D model according to some embodiments.
Figure 14B:
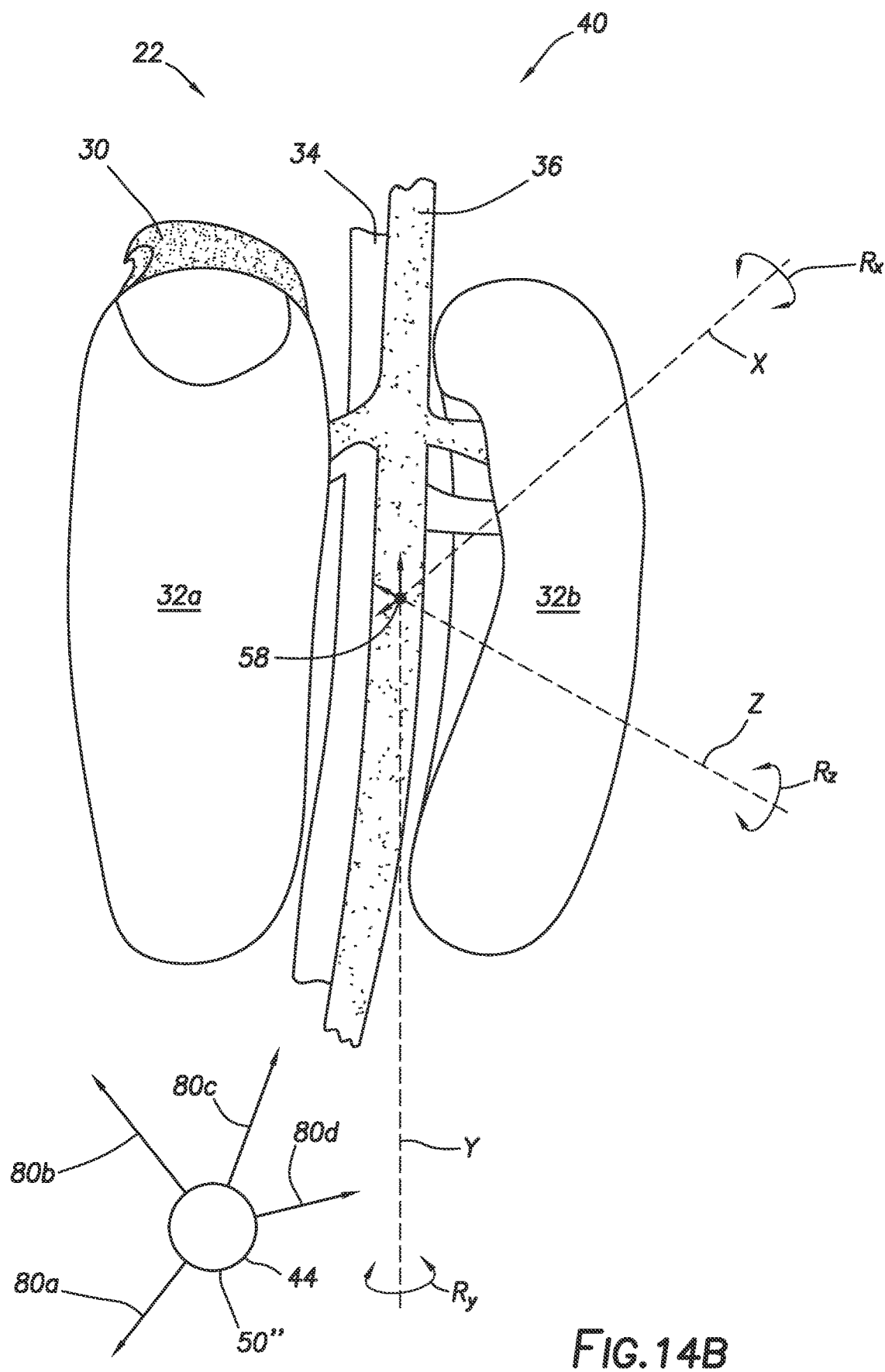

Referring to FIG. 14A-B, an image 22 of components of a 3D model 40 is shown with a center of rotation 58 of the components 30, 32a, 32b, 34, 36. FIG. 14A is similar to the image 22 shown in FIG. 9. The center of rotation 58 is determined by a virtual rectangular prism with its boundaries determined by the outermost edges of the components of the 3D model that have a transparency of less than 100% (components 30, 32a, 32b, 34, 36 in this example) such that all the components are within the virtual rectangular prism. The center of rotation 58 is the center of the volume of the virtual rectangular prism. The group of the components 30, 32a, 32b, 34, 36 can be rotated via user interactions with the touchscreen 20. The 3D model 40 has three Cartesian axes X, Y, Z that intersect at the center of rotation 58. The 3D model 40 can be rotated in three degrees of rotational motion (e.g., rotation about the X, Y, Z Cartesian axes) by the interactions of the user with the touchscreen 20.

For example, FIG. 14A illustrates an interaction with the touchscreen 20 to rotate the image 22 about Y axis (rotation Ry). A first input can be provided at location 50 of the touchscreen 20 by the user and detected by the computing device 16. The computing device 16 can indicate the detection by displaying the icon 44 on the touchscreen 20 at the location 50. As the input is moved (movement 78) from right to left to position 50', the computing device 16 tracks the input across the touchscreen 20 by displaying the icon 44 at the current location of the input. The image 22 can rotate about the Y axis in response to the movement 78 of the input. FIG. 14B shows a resulting image 22 after the input has been moved to the location 50'. If movement of the input is then made from the location 50' in any of the directions 80a-d (as well as any other direction not indicated), the image 22 will respond by rotating about the center of rotation 58 in the desired rotation. Therefore, if the user wishes to view the tumor 30 from various points of view, then the user can simply interact with the touchscreen 20 to rotate the image 22 as desired around the center of rotation 58.

Figure 15A:
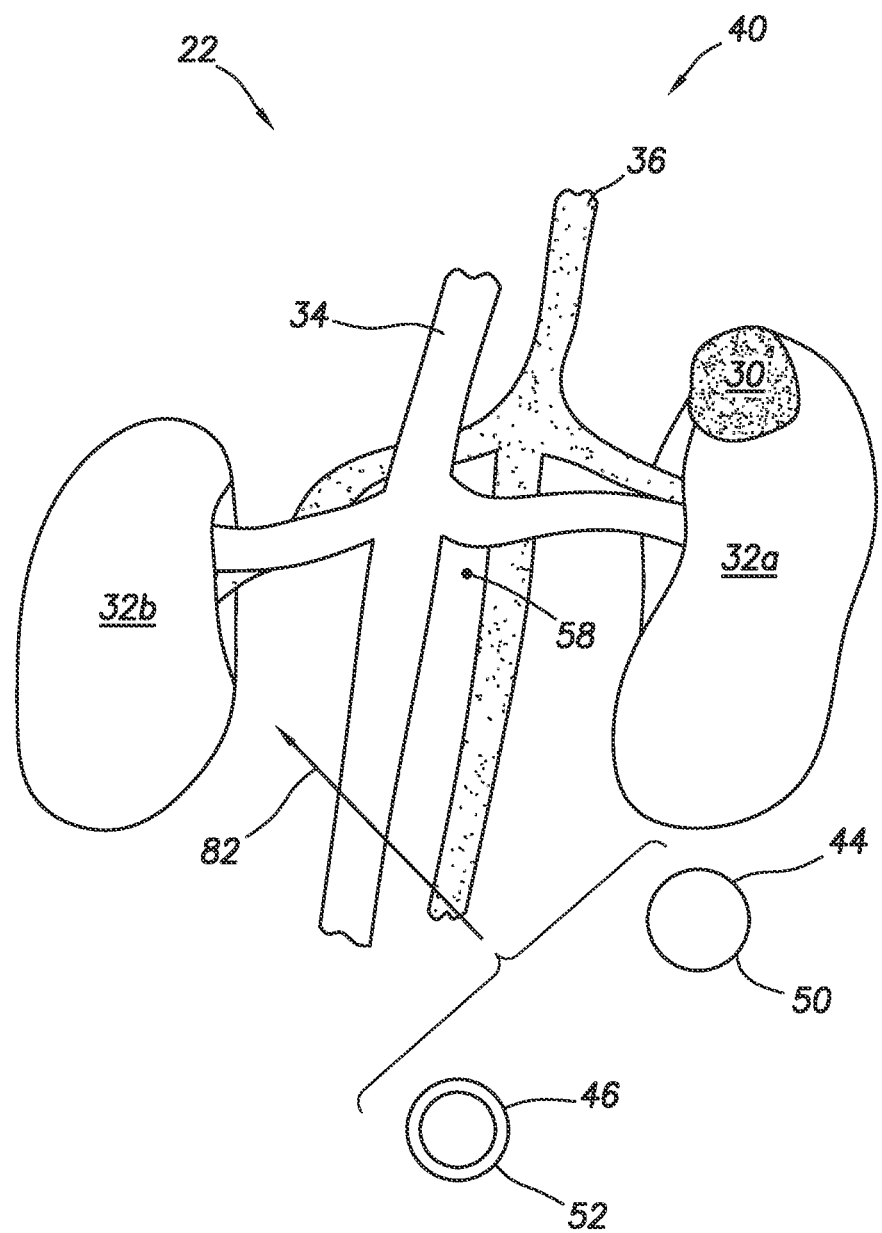
FIGS. 15A-15B are representative perspective views of components of a 3D model (in this example, a 3D rendering of human organs) as seen on a touchscreen user interface as well as interactions for lateral movement the 3D model according to some embodiments.

Additionally, if the user wishes to reposition the components 30, 32a, 32b, 34, 36 of the 3D model 40 in the image 22, then the user can apply first and second inputs simultaneously to the touchscreen 20 as indicated in FIG. 15A. The first input applied at location 50 can be detected by the computing device 16, which can display the icon 44 at the location 50. The second input applied at location 52 can be detected by the computing device 16, which can display the icon 46 at the location 52. These icons 44, 46 may be different so the user can easily distinguish them from each other, however, it is not a requirement that they be different. The icon 44 is again shown as a ring icon, but it can also be any other suitable shape. The icon 46 is shown as a double concentric ring icon, but it can also be any other suitable shape. Movement 82 of the first and second inputs across the touchscreen 20 can cause the computing device 16 to linearly translate the components 30, 32a, 32b, 34, 36 to a new position in the image 22, as seen in FIG. 15B.

Figure 15B:
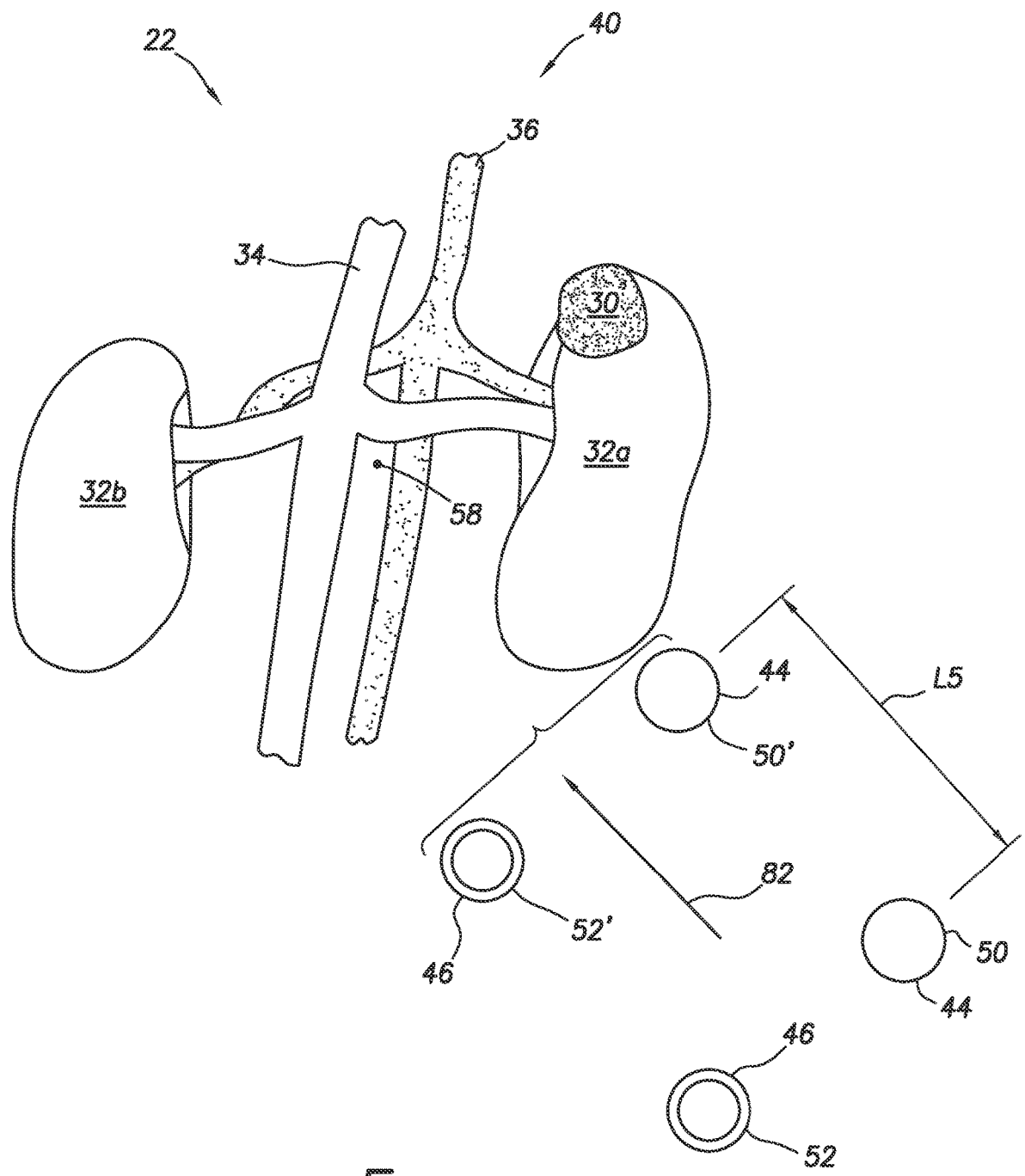

Referring to FIG. 15B, the first and second inputs have been moved simultaneously (movement 82) a distance of L5 across the touchscreen 20 to new locations 50' and 52', respectively, without significant movement of each of the inputs toward each other. This movement 82 can be detected by the computing device 16 and cause the computing device 16 to linearly move the components 30, 32a, 32b, 34, 36 in the image a corresponding distance L5. The computing device 16 can mirror the movement of the components 30, 32a, 32b, 34, 36 in the image 22 with the movement of the first and second inputs on the touchscreen 20. Therefore, if the first and second inputs are moved in a circular motion, the computing device 16 can cause the components 30, 32a, 32b, 34, 36 to move in a correspondingly circular motion in the image 22. If the spacing between the inputs is maintained, then the components 30, 32a, 32b, 34, 36 will only be translated around in the image 22. However, if the distance between the two inputs is increased or decreased, then not only will the components 30, 32a, 32b, 34, 36 be translated around in the image 22, but the image will also be zoomed in or out depending upon whether the distance is increased or decreased, respectively.

Figure 16A:
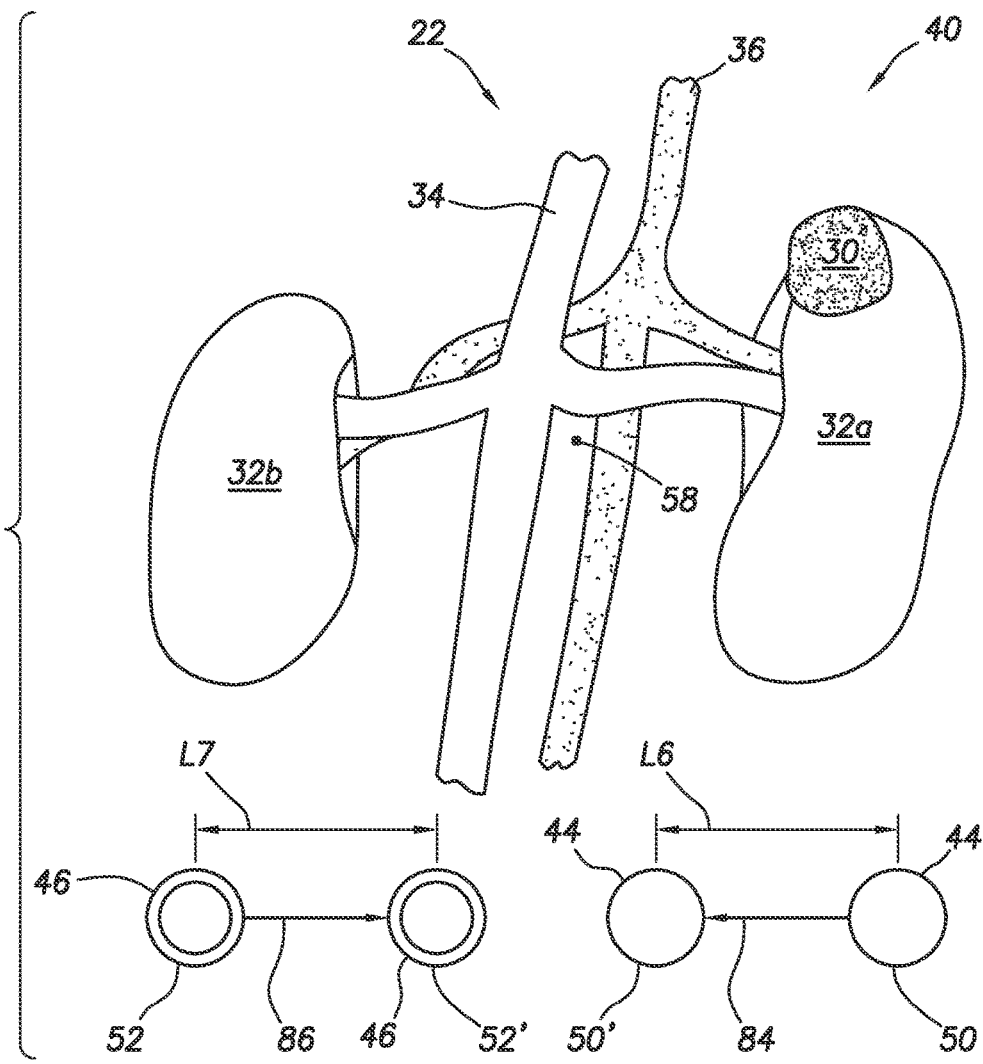
FIGS. 16A-17B are representative perspective views of components of a 3D model (in this example, a 3D rendering of human organs) as seen on a touchscreen user interface as well as interactions for zooming in and out the image of the 3D model according to some embodiments.
Figure 16B:
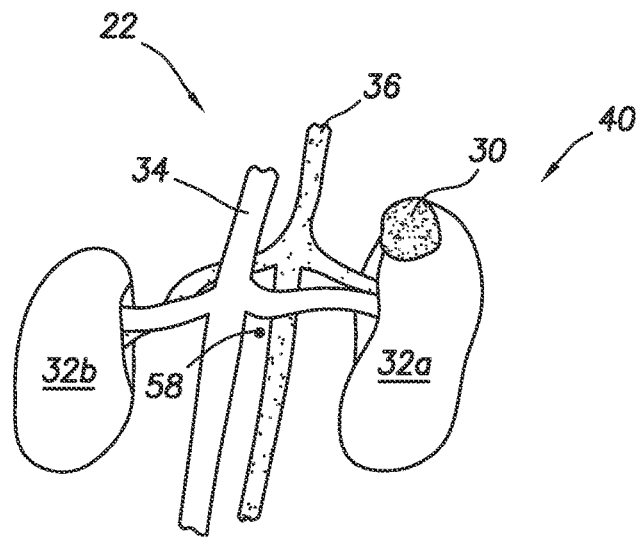

FIGS. 16A-17B illustrate user interactions with the touchscreen 20 to cause the image 22 of the components 30, 32a, 32b, 34, 36 to be zoomed out or zoomed-in, wherein zoomed out reduces the size of the components 30, 32a, 32b, 34, 36 in the image 22, and zoomed-in enlarges the size of the components 30, 32a, 32b, 34, 36 in the image 22. FIG. 16A shows the components 30, 32a, 32b, 34, 36 in the image 22 prior to being zoomed-out in response to user interactions with the touchscreen 20. The user can simultaneously apply first and second inputs to the touchscreen 20 at locations 50 and 52, respectively. The computing device 16 can detect the first and second inputs and display the icons 44 and 46 at the locations 50 and 52, respectively, to indicate the detections. Movement 84 of the first input a distance L6 along the touchscreen 20 toward the second input to a location 50' and movement 86 of the second input a distance of L7 along the touchscreen 20 toward the first input to a location 52' can be detected by the computing device 16, which will cause the components 30, 32a, 32b, 34, 36 in the image 22 to reduce their size a corresponding amount in response to the movements 84, 86 of the first and second inputs. Further reduction of the components 30, 32a, 32b, 34, 36 can be performed by moving the inputs even closer together. The components 30, 32a, 32b, 34, 36 reduced in size as a result of the movements 84, 86 of the first and second inputs are shown in FIG. 16B.

Figure 17A:
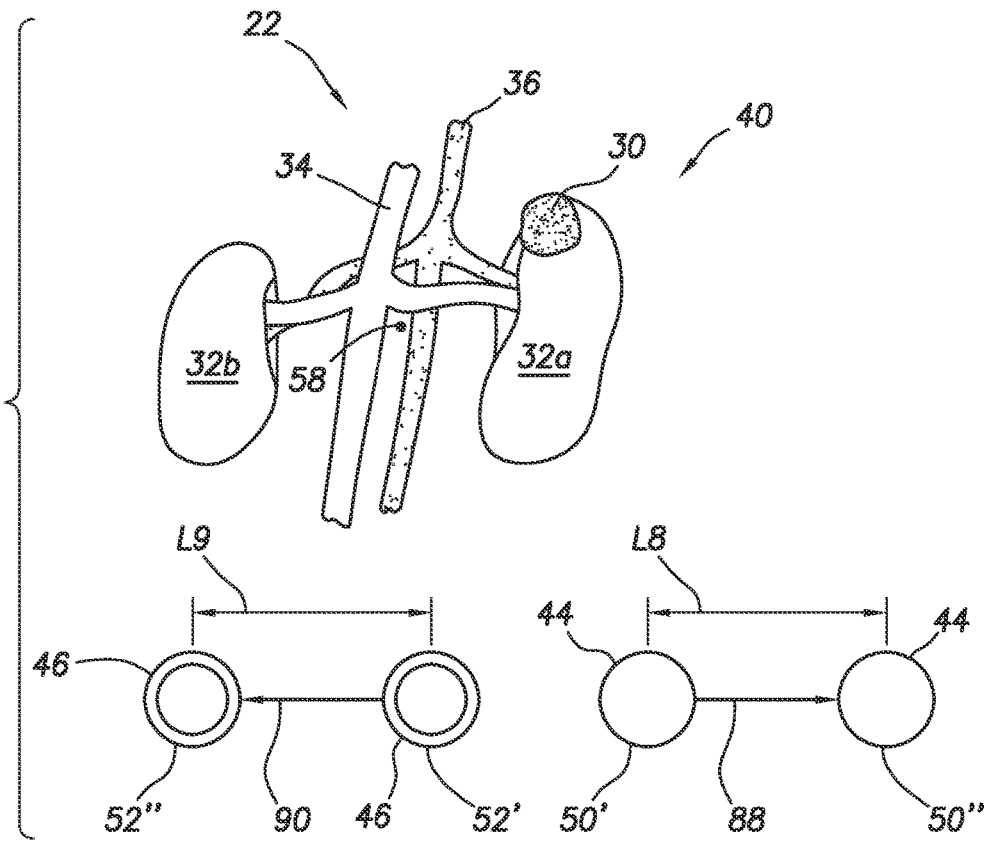
Figure 17B:
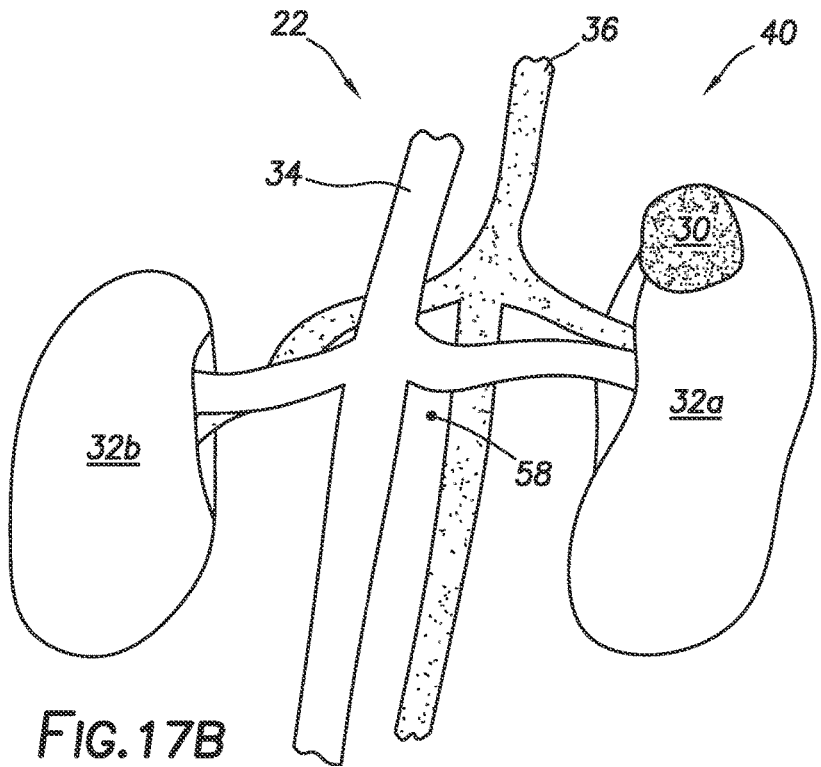

Similarly, reversing the interactions shown in FIG. 16A can result in enlarging the components 30, 32a, 32b, 34, 36 in the image 22, as shown in FIGS. 17A-17B. FIG. 17A shows the components 30, 32a, 32b, 34, 36 in the image 22 prior to being zoomed-in as a response to user interactions with the touchscreen 20. The user can simultaneously apply first and second inputs to the touchscreen 20 at locations 50' and 52', respectively. The computing device 16 can detect the first and second inputs and display the icons 44 and 46 at the locations 50' and 52', respectively, to indicate the detections. Movement 88 of the first input a distance L8 along the touchscreen 20 away from the second input to a location 50" and movement 90 of the second input a distance of L7 along the touchscreen 20 away from the first input to a location 52" can be detected by the computing device 16, which will cause the components 30, 32a, 32b, 34, 36 in the image 22 to enlarge their size a corresponding amount in response to the movements 88, 90 of the first and second inputs. Further enlargement of the components 30, 32a, 32b, 34, 36 can be performed by moving the inputs even farther apart. The components 30, 32a, 32b, 34, 36 enlarged in size as a result of the movements 88, 90 of the first and second inputs are shown in FIG. 17B.

Figure 18A:
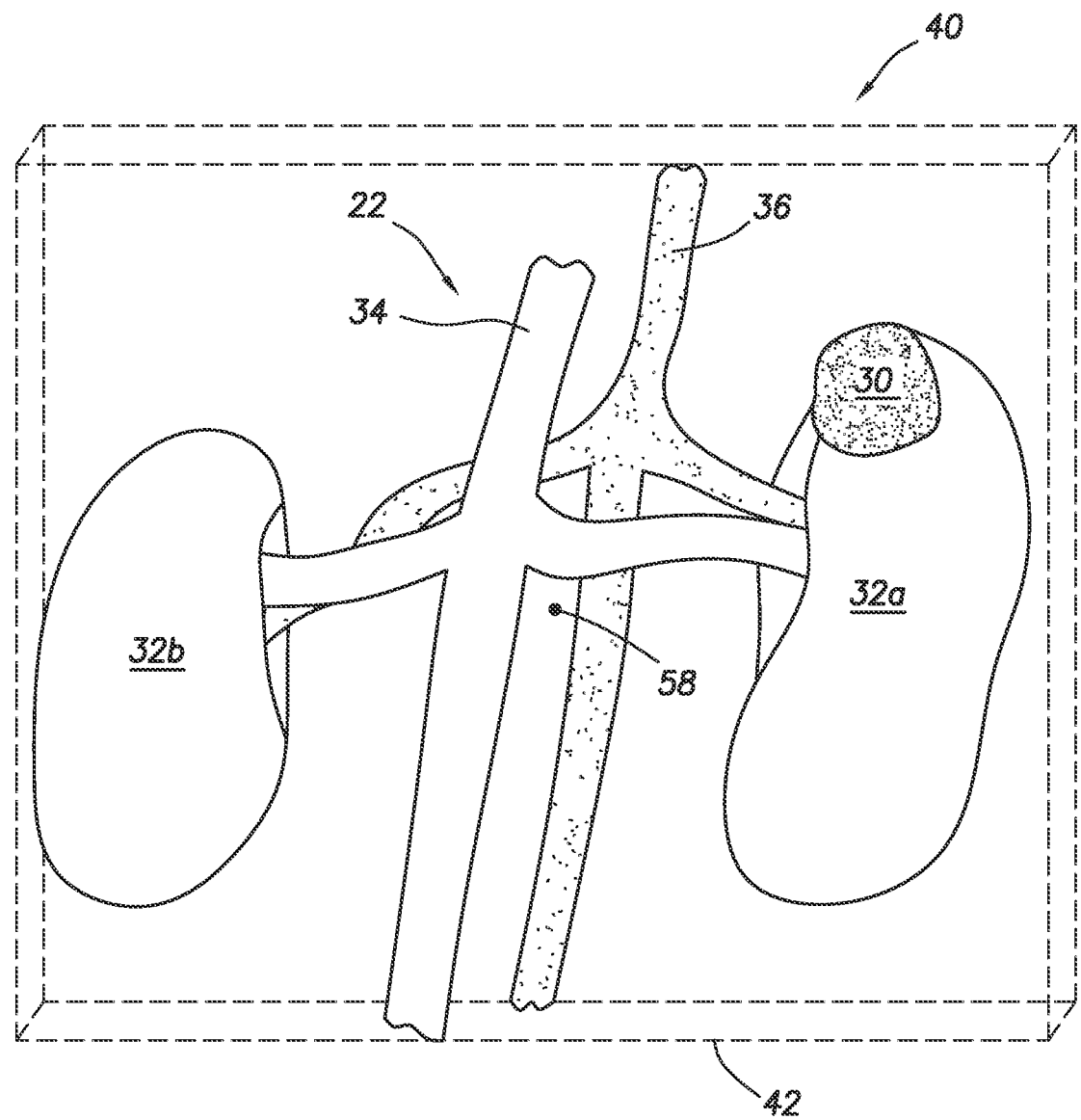
FIGS. 18A-18F are representative perspective views of components of a 3D model (in this example, a 3D rendering of human organs) as seen on a touchscreen user interface of changing a center of rotation of the image by changing a transparency of components of the 3D model according to some embodiments.

FIGS. 18A-18F illustrate automatically adjusting the center of rotation 58 of the components with less than 100% transparency (i.e., the components that are visible). FIG. 18A shows the components 30, 32a, 32b, 34, 36, which in this example are the only components of the 3D model 40 that have a transparency of less than 100%. As described above, the center of rotation 58 of the components 30, 32a, 32b, 34, 36 is determined by forming a virtual rectangular prism 42 around the components, with the outer edges of the components 30, 32a, 32b, 34, 36 determining the boundaries of the rectangular prism 42, and thereby determining the center of rotation 58. When the transparency of the components is changed from being less than 100% to being equal to 100%, then the center of rotation 58 can change, that is if the rectangular prism 42 is changed by the transparency changes.

Figure 18B:
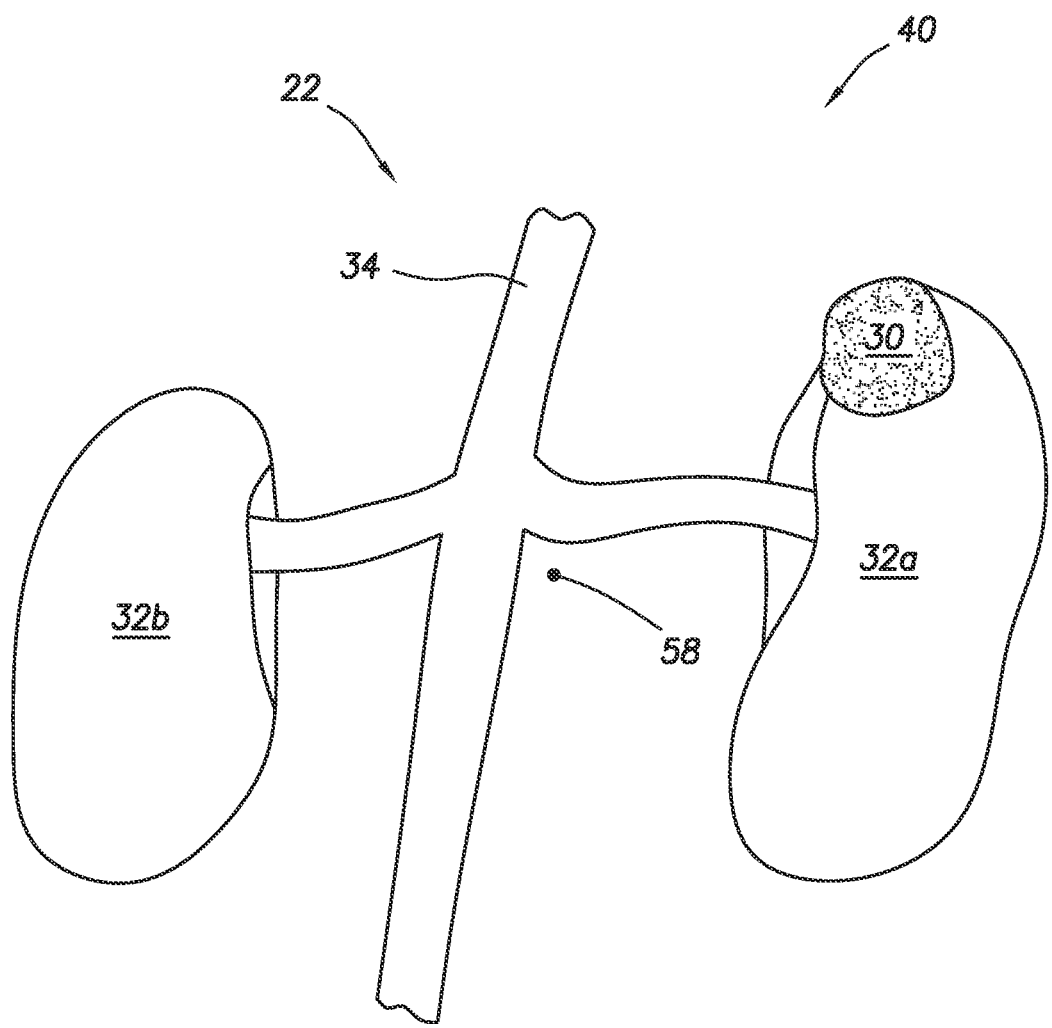
Figure 18C:
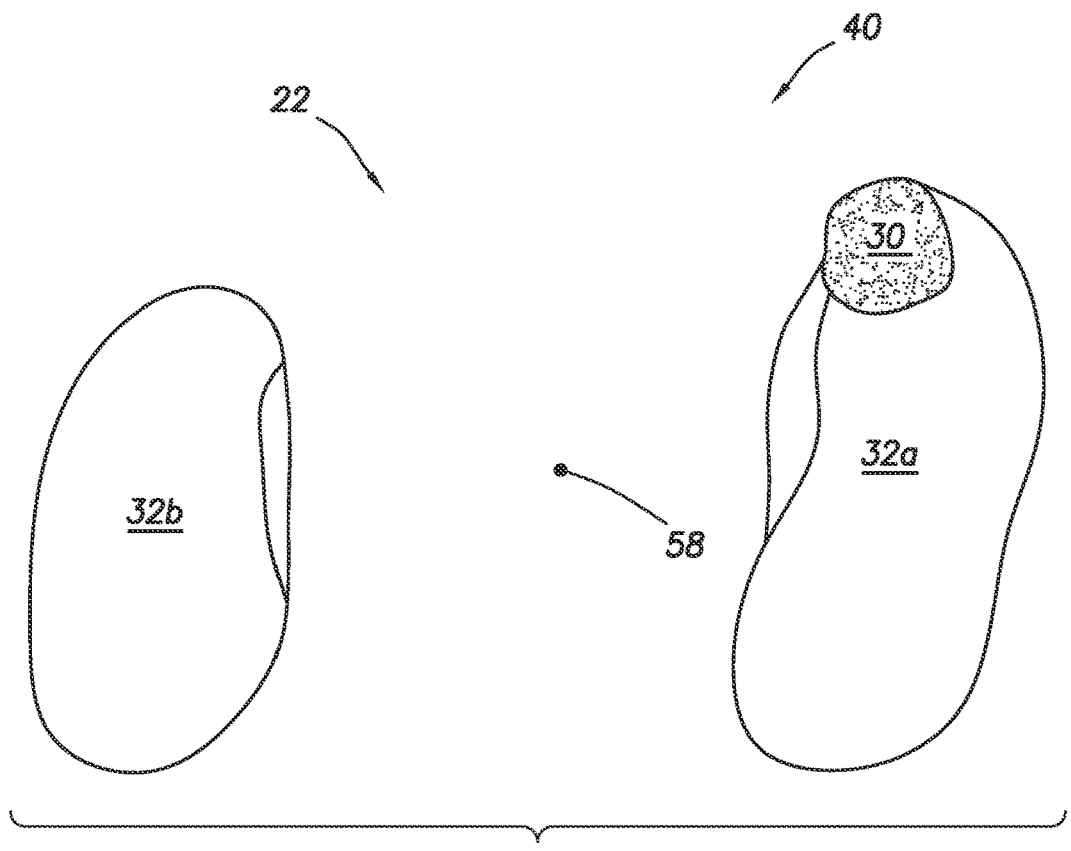
Figure 18D:
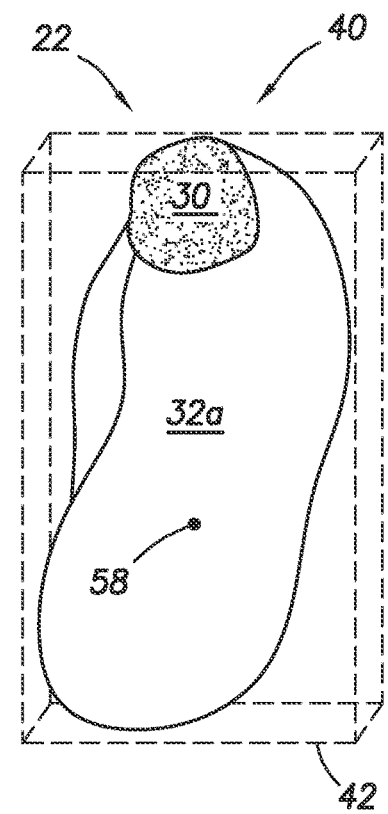

Referring to FIG. 18B, the transparency of the component 36 has been changed to be equal to 100% (i.e., made invisible), with the image 22 only displaying the components 30, 32a, 32b, 34. Since the rectangular prism 42 (not shown in this figure) is only slightly changed, then the center of rotation 58 remains very close to the previous center of rotation 58 shown in FIG. 18A. Referring to FIG. 18C, the transparency of the component 34 has been changed to be equal to 100% (i.e., made invisible), with the image 22 only displaying the components 30, 32a, 32b. Since the rectangular prism 42 (not shown in this figure) is again only slightly changed, then the center of rotation 58 remains fairly close to the previous centers of rotation 58 shown in FIGS. 18A and 18B. However, referring to FIG. 18D, the transparency of the component 32b has been changed to be equal to 100% (i.e., made invisible), with the image 22 only displaying the components 30, 32a. Since the bounding rectangular prism 42 is significantly different (e.g., smaller, offset) than FIGS. 18A, 18B, and 18C, then the center of rotation 58 of FIG. 18D is also substantially changed from those in FIGS. 18A, 18B, and 18C. In FIG. 18D, the center of rotation may correspond to the center of the mass formed by the components 30, 32a. Therefore, user interactions with the touchscreen 20 as described in reference to FIGS. 14A-14B, will apply to the components in FIG. 18D, by rotating the components 30, 32a about the new center of rotation 58.

Figure 18E:
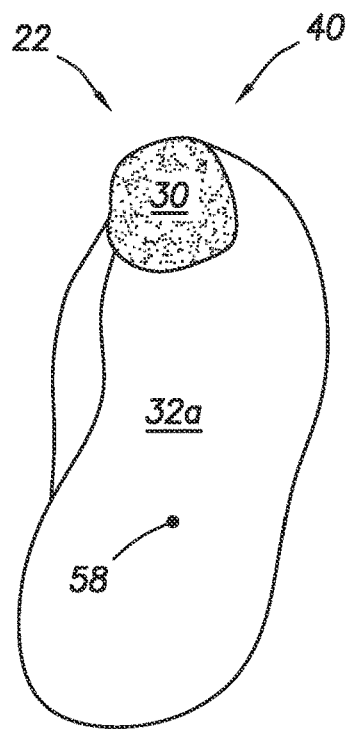
Figure 18F:
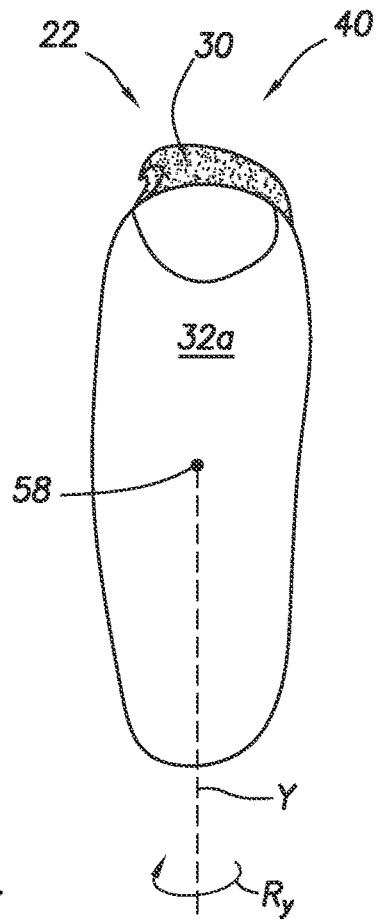

With reference to FIGS. 18E-18F, the displayed components 30, 32a in the image 22 can be rotated about the new center of rotation 58. As described above with reference to FIG. 14A, a first input can be provided at location 50 of the touchscreen 20 by the user and detected by the computing device 16. The computing device 16 can indicate the detection by displaying the icon 44 on the touchscreen 20 at the location 50. As the input is moved (movement 78) from right to left to position 50', the computing device 16 tracks the input across the touchscreen 20 by displaying the icon 44 at the current location of the input. The image 22 can rotate about the Y axis in response to the movement 78 of the input. In the example shown in FIGS. 18E-18F, the difference from the FIG. 14A is that the components in the image 22 are fewer than the components included in the image 22 in FIG. 14A.

When the user desires to add back components to the image 22, an input can be applied to a location on the touchscreen away from any components, thus causing a component list to be displayed that contains the components of the 3D model 40, even those components that have a transparency set to equal 100%. By selecting a component in the list, the user can select whether to change the component's transparency from 100% to less than 100%, thereby causing the image 22 to include the newly viewable component, which can also cause the center of rotation 58 to change based on a new rectangular prism bounded by the new set of components.

If a user wishes to delete a 3D model 40, a predetermined delay period may be applied before the deletion is completed to allow the user to abort the deletion process. The delay period may be accompanied by a visual or audible countdown, fade sequence, or timer. The deletion process may be aborted, for example, by a predefined abort motion such as shaking detectable via the gyroscope of the device 16.

FIG. 19 illustrates a sequence of deleting the 3D model 40 from the visualization tool 10. Operation 100 shows an entry in a list of 3D models (3D model 40 identified by displayable text 106). Only the one entry is shown in operation 100, but multiple list items can be provided in the list of 3D models stored in the visualization tool 10. To select the entry shown in operation 100, a first touchscreen input is provided and detected within the screen area bounded by the list item being displayed on the touchscreen 20. The 3D model is selected in response to the first touchscreen input and the tool 10 indicates the detection by changing an icon and displayable text to indicate to the user that the item is selected. In this example, the icon changes from an outlined box to a box filled with a different color, but any change in the icon can be used to indicate the selection. In this example, displayable text "ARE YOUR SURE?" is displayed to communicate that the first touchscreen input has been detected and the list item is ready to receive confirmation to delete the entry. A second touchscreen input can then be provided and detected within the screen area bounded by the list item being displayed on the touchscreen 20. It should be understood that the receptive portion of the touchscreen 20 for receiving the first and second touchscreen inputs can be a subset of the area bounded by the displayed list item, or a separate area of the touchscreen 20 designated for such inputs.

The second touchscreen input causes the list item icon to change to an "undo" icon (e.g. a box with a circle arrow within the box), with the displayable text associated with the icon displaying a value of a countdown timer and the text "UNDO." In operation 102, the displayable text shows "UNDO" and the countdown timer value shows "4 s" to indicate 4 seconds remaining before deletion is complete. This countdown timer can be any units of time, but seconds is the preferred time unit. As can be seen in operation 102, the displayable text 106 is still very readable. As the deletion process continues the brightness and color of the item being deleted fades in synchronization with the countdown timer. In operation 104, three seconds have passed since operation 102 with the timer indicating one second left before deletion of the 3D model 40 is complete. The displayable text 106 has significantly faded to provide a visual indication to the user that the 3D model 40 is about to be deleted. After the last second has passed, then the 3D model 40 is deleted from the list and deleted from the visualization tool 10. The deletion process may be aborted, for example, by a predefined abort process such as providing a third touchscreen input within the screen area bounded by the list item displayed on the touchscreen 20 before the last second has passed.

In alternative embodiments, the deletion process may be aborted, for example, by a predefined abort motion such as shaking detectable via a gyroscope of the visualization tool 10. As an example, the surgeon S may shake the visualization tool 10 for a period of time of more than one second, or the surgeon S may use two quick movements to move the visualization tool 10 in opposite directions to shake the visualization tool 10. It is to be understood that the surgeon S may shake the visualization tool 10 for any other duration of time.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
    accessing a three-dimensional (3D) model of an object with a visualization tool having a touchscreen, the 3D model comprising first and second components;
    displaying, via the touchscreen, an image of the first and second components;
    detecting a first contact based input at the touchscreen;
    selecting the first component in response to the first contact based input;
    displaying a first icon on the touchscreen, the first icon representing a location on the touchscreen of the first contact based input;
    displaying second and third icons on the touchscreen in response to detecting movement of the first contact based input along the touchscreen;
    tracking movement of the first icon with the movement of the first contact based input;
    determining from the tracked movement that the first icon at least partially overlaps one of the second and third icons;
    selecting a display parameter of the first component in response to the overlap determination;
    detecting a second contact based input at the touchscreen; and
    adjusting the selected display parameter in response to a detected movement of the second contact based input along the touchscreen.

2. The method of claim 1, wherein the selecting the first component includes generating a haptic signal.

3. The method of claim 1, further comprising displaying a fourth icon in response to the second contact based input, the fourth icon representing a location on the touchscreen of the second contact based input, wherein the fourth icon tracks the movement of the second contact based input along the touchscreen.

4. The method of claim 1, wherein the 3D model comprises a third component which corresponds to a cross-sectional area of the 3D model, wherein the visualization tool displays the third component along with a cross-sectional portion of each of the first and second components, and wherein the cross-sectional portion of each of the first and second components also corresponds to the cross-sectional area of the 3D model.

5. The method of claim 4, wherein the adjusting the selected display parameter includes adjusting windowing of the third component.

6. The method of claim 5, wherein the movement of the second contact based input comprises movement in a first direction and adjusts the windowing of the third component in one way based on the movement in the first direction, and wherein the movement of the second contact based input comprises movement in a second direction and adjusts the windowing of the third component in another way based on the movement in the second direction.

7. The method of claim 1, wherein the adjusting the selected display parameter includes adjusting a transparency of the first component.

8. The method of claim 7, wherein the transparency of the first component is adjustable between 0% and 100% based on the detected movement of the second contact based input.

9. The method of claim 8, wherein a center of rotation of the 3D model is changed in response to the transparency of the first component being adjusted to 100%.

10. The method of claim 1, wherein the second icon represents a first adjustable display parameter and the third icon represents a second adjustable display parameter.

11. The method of claim 1, wherein the displaying the second and third icons includes displaying the third icon to be visually different from the second icon.

* * * * *